United States Patent
Issakani et al.

(10) Patent No.: US 6,740,495 B1
(45) Date of Patent: May 25, 2004

(54) UBIQUITIN LIGASE ASSAY

(75) Inventors: Sarkiz D. Issakani, San Jose, CA (US); Jianing Huang, Foster City, CA (US); Julie Sheung, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/542,497

(22) Filed: Apr. 3, 2000

(51) Int. Cl.[7] ................................................. G01N 33/53
(52) U.S. Cl. .................... 435/7.92; 435/7.4; 435/7.1; 435/7.6; 435/7.9; 435/7.91; 435/7.95; 435/14; 435/21; 435/28; 435/29; 435/320.1; 435/325; 436/546; 436/544; 436/164; 436/172; 436/805; 536/24.5; 536/23.1; 536/23.2; 536/23.5
(58) Field of Search .................... 435/7.4, 7.1, 7.6, 435/7.9, 7.91, 7.95, 14, 21, 28, 7.92, 29, 320.1, 325; 436/546, 544, 164, 172, 805; 536/24.5, 23.1, 23.2, 23.5

(56) References Cited

U.S. PATENT DOCUMENTS

| | | | | |
|---|---|---|---|---|
| 5,726,025 | A | * | 3/1998 | Kirschner et al. |
| 5,952,481 | A | * | 9/1999 | Markham et al. |
| 5,968,747 | A | * | 10/1999 | Hillman et al. |
| 5,968,761 | A | * | 10/1999 | Rolfe et al. |
| 5,976,849 | A | * | 11/1999 | Hustad et al. |
| 5,997,856 | A | * | 12/1999 | Hora et al. |
| 6,001,619 | A | * | 12/1999 | Beach et al. |
| 6,057,112 | A | * | 5/2000 | Bandman et al. |
| 6,087,122 | A | * | 7/2000 | Hustad et al. |
| 6,146,624 | A | * | 11/2000 | Lal et al. |
| 6,306,663 | B1 | * | 10/2001 | Kenten et al. |

FOREIGN PATENT DOCUMENTS

| | | |
|---|---|---|
| CA | 2269099 | 5/1998 |
| EP | 0 587 279 | 3/1999 |
| EP | 1 033 401 | 9/2000 |
| WO | 98/21326 | 5/1998 |
| WO | 99/06553 | 2/1999 |
| WO | 99/06554 | 2/1999 |
| WO | 99/32514 | 7/1999 |
| WO | 99/34012 | 7/1999 |
| WO | 00/22110 | 4/2000 |
| WO | 00/50445 | 8/2000 |
| WO | 00/58472 | 10/2000 |

OTHER PUBLICATIONS

Tan, et al., "Recruitement of a ROC1–CUL1 Ubiquitin Ligase by Skp1 and HOS to Catalyze the Ubiquitination of IκBα," *Mol. Cell*, 3(4):527–533 (1999).

Ohta, et al., "ROC1, a Homolog of APC11, Represents a Family of Cullin Partners with an Associated Ubiquitin Ligase Activity,", *Mol. Cell* 3(4):535–541(1999).

Hershko, A., "Roles of ubiquitin–mediated proteolysis in cell cycle control,", *Curr, Opin. Cell Biol.* 9:788–799 (1997).

Spencer, et al., "Signal–Induced ubiquitination of IκBα by the F–box protein Slimb/β–TrCP," *Genes Dev.* 13:284–294 (1999).

Kamura et al., "Rbx1, a Component of the VHL Tumor Suppressor Complex and SCF Ubiquitin Ligase," *Science* 284:657–661 (1999).

Yu et al., "Identification of a cullin homology region in a subunit of the anaphase–promoting complex", *Science* 279:1219–1222 (1998).

Duan et al., SAG, a novel zinc RING finger protein that protects cells from apoptosis induced by redox agents, *Mol. Cell. Biol.* 19:3145–3155 (1999).

(List continued on next page.)

*Primary Examiner*—Christopher L. Chin
*Assistant Examiner*—Pensee T. Do
(74) *Attorney, Agent, or Firm*—Townsend and Townsend and Crew LLP

(57) ABSTRACT

The invention relates to assays for measuring ubiquitin ligase activity and for identifying modulators of ubiquitin ligase enzymes.

19 Claims, 12 Drawing Sheets

OTHER PUBLICATIONS

Son et al., "Protein–kinase CKII interacts with and phosphorylates the SAG protein containing ring–H2 finger motif", *Biochem. Biophys. Res. Comm.* 263:743–748 (1999).

Kipreous et al., "cul–1 is required for cell cycle exit in *C. elegans* and identifies a novel gene family," *Cell* 85:829–839 (1996).

* cited by examiner

FIGURE 8A

```
atgtccagctcgccgctgtccaagaaacgtcgcgtgtccgggcctgatccaaagccgggttctaactgctcccctgccca
gtccgtgttgccccaagtgccctcggcgccaaccaacggaatggcgaagaacggcagtgaagcagacatcgatgagggcc
tttactcccggcagctgtatgtgttgggccatgaggcgatgaagcggctccagacatccagcgttctggtgtcaggcctg
cggggcctgggggtagagatcgcgaagaacatcatccttggcggggtcaaggccgtgaccctccatgaccagggcacggc
ccagtgggctgacctctcctcccagttctacctgcgagaggaggacataggga aaaaccgcgctgaggtgtcacagcccc
gccttgctgaactcaatagctacgtgcctgtcaccgcctacactgggccgctggttgaggacttcctcagtggcttccag
gtggtggtcctcactaacagcccctggaggaccagctgcgcgtgggcgagttctgtcatagccgtggcatcaagctggt
agtggcagacacgagaggcttgtttgggcaactcttctgcgactttggagaggaaatgatcctcacagattccaacgggg
agcagcccctcagcaccatggtttctatggtcaccaaggacaaccctggtgtggttacctgcctggatgagcccgacat
gggtttgagagtggcgattttgtttccttctccgaagtacagggcatgactgagctcaatggaaaccagcccatagagat
caaagtcctgggtccttacacctttagcatctgtgacacctccaacttctccgattacatccgtggaggcattgtcagcc
aggtcaaagtacctaagaagataagctttaaatccttgtcagcctcgctggcagagcctgactttgtgatgacggacttc
gccaagtttt ctcgccccgctcagcttcacattggcttccaggccttgcacaagttctgtgcacagcacagccggccacc
tagaccccggaacgaggaggatgcagcagagctggtgaccctagcacgcgctggtgaactctaaagcctcgtcggcagtgc
agcaagatagcctggatgaggacctcatccggaacctggcctttgtggcagccggggacctggcgcccatcaatgccttc
attggggcctggctgcccaggaagtcatgaaggcctgctctgggaagtttatgcccatcatgcagtggctgtactttga
tgcccttgagtgtctcccggaggacaaagaatccctcacagaggacaagtgcctcccgcgccagaaccgttatgatgggc
aggtggctgtgtttggctcagacctgcaagagaagctgggcaggcagaagtacttcctggtgggtgcagggg ctattggc
tgtgagctgctcaagaactttgccatgattgggctgggctgtggtgagaacggagaaataattgtcacagacatggacac
cattgagaaatctaatctgaaccgacagtttctattccggcctgggatgtcacgaagttaaatctgacacagctgctg
cagctgtgcaccagatgaatccacatatccgggtgacaagccaccagaaccgtgtgggtcctgacactgaacgtatctac
gacgacgatttcttccaaactctggatggcgtggccaacgccttagacaacgtggatgcccgcatgtacatggaccgccg
ctgcgtgtactaccggaagccgctgctcgaatcaggcgaccctgggcaccaagggcaacgtccaggtggtgatcccctt cc
tgacagagtcctacagctccagccaagacccacctgagaagtccatccccatctgtaccctgaagaacttcccc aacgcc
atcgaacacactcttcagtgggctcgggatgaatttgaaggcctcttcaagcagccagcggaaaatgtcaaccagtacct
cacagaccctaagtttgtggagcggacattgcggctggcgggtacccagccactggaggtgctggaggctgtgcagcgca
gctggtgctgcagctaccgcagagctgggcagactgtgtgacctgggcctgccaccactggcacacccagtattctaac
aatatccggcagctgttgcacaacttccctcccgaccagctcacaagctcgggagctccttctggtctgggcccaaacg
ttgtcctcacccactcacctttgatgttagcaaccctctgcatctggactatgtgatggctgctgccaacctgtttgccc
agacctacgggctggcaggctctcaggaccgagctgctgtggccacactcctgcagtctgtacaggtccccgagtttacc
cccaagtctggcgtcaaaatccacgtttctgaccaggagctgcagagcgccaatgcttctgttgacgacagccgtttaga
ggagctcaaggctacgctgcctagccccgacaagctccctggattcaagatgtacccattgactttgagaaggatgatg
atagtaactttcacatggacttcattgtggccgcatccaacctccgggccgaaaactatgacattcccctgcagaccgg
cacaagagcaagctgattgcagggaagatcatcccagccattgccacgaccacagcagctgtcgttggccttgtgtgtct
ggagctgtacaaggtagtgcagggacaccgacacctcgactcctacaagaatggtttcctcaacctggccctgccgtttt
tcggtttctctgaacctctggctgcaccacgtcaccagtactataaccaagagtggacattgtgggatcgctttgaggtt
cagggactgcagcccaacggtgaggagatgaccctcaaacaattcctcgactactttaagacagagcacaaattggagat
taccatgctgtcccagggtgtgtccatgctctattccttctttatgccagctgcgaagctcaaggaacggttggaccagc
cgatgacagagattgtaagccgtgtgtcgaagcgaaagctgggccgccacgtgcgggcgctggtgcttgagctgtgctgc
aacgacgagagcggcgaggacgtcgaagtcccctacgtccgatataccatccgttaa
```

FIGURE 8B

```
MSSSPLSKKRRVSGPDPKPGSNCSPAQSVLPQVPSAPTNGMAKNGSEADIDEGLYSRQLYVLGHEAMKRLQTSSVLVSGL
RGLGVEIAKNIILGGVKAVTLHDQGTAQWADLSSQFYLREEDIGKNRAEVSQPRLAELNSYVPVTAYTGPLVEDFLSGFQ
VVVLTNSPLEDQLRVGEFCHSRGIKLVVADTRGLFGQLFCDFGEEMILTDSNGEQPLSTMVSMVTKDNPGVVTCLDEARH
GFESGDFVSFSEVQGMTELNGNQPIEIKVLGPYTFSICDTSNFSDYIRGGIVSQVKVPKKISFKSLSASLAEPDFVMTDF
AKFSRPAQLHIGFQALHKFCAQHSRPPRPRNEEDAAELVTLARAVNSKASSAVQQDSLDEDLIRNLAFVAAGDLAPINAF
IGGLAAQEVMKACSGKFMPIMQWLYFDALECLPEDKESLTEDKCLPRQNRYDGQVAVFGSDLQEKLGRQKYFLVGAGAIG
CELLKNFAMIGLGCGENGEIIVTDMDTIEKSNLNRQFLFRPWDVTKLKSDTAAAAVHQMNPHIRVTSHQNRVGPDTERIY
DDDFFQTLDGVANALDNVDARMYMDRRCVYYRKPLLESGTLGTKGNVQVVIPFLTESYSSSQDPPEKSIPICTLKNFPNA
IEHTLQWARDEFEGLFKQPAENVNQYLTDPKFVERTLRLAGTQPLEVLEAVQRSLVLQLPQSWADCVTWACHHWHTQYSN
NIRQLLHNFPPDQLTSSGAPFWSGPKRCPHPLTFDVSNPLHLDYVMAAANLFAQTYGLAGSQDRAAVATLLQSVQVPEFT
PKSGVKIHVSDQELQSANASVDDSRLEELKATLPSPDKLPGFKMYPIDFEKDDDSNFHMDFIVAASNLRAENYDIPPADR
HKSKLIAGKIIPAIATTTAAVVGLVCLELYKVVQGHRHLDSYKNGFLNLALPFFGFSEPLAAPRHQYYNQEWTLWDRFEV
QGLQPNGEEMTLKQFLDYFKTEHKLEITMLSQGVSMLYSFFMPAAKLKERLDQPMTEIVSRVSKRKLGRHVRALVLELCC
NDESGEDVEVPYVRYTIRZ
```

FIGURE 9A

ATGGCGCTGAAACGGATTAATAAGGAACTTAGTGATTTGGCCCGTGACCCTCCAGCACAATGTTCTGCAGGTCCAGTTGG
GGATGATATGTTTCATTGGCAAGCCACAATTATGGGACCTAATGACAGCCCATATCAAGGCGGTGTATTCTTTTTGACAA
TTCATTTTCCTACAGACTACCCCTTCAAACCACCTAAGGTTGCATTTACAACAAGAATTTATCATCCAAATATTAACAGT
AATGGCAGCATTTGTCTCGATATTCTAAGATCACAGTGGTCGCCTGCTTTAACAATTTCTAAAGTTCTTTTATCCATTTG
TTCACTGCTATGTGATCCAAACCCAGATGACCCCCTAGTGCCAGAGATTGCACGGATCTATAAAACAGACAGAGATAAGT
ACAACAGAATATCTCGGGAATGGACTCAGAAGTATGCCATGTGA

FIGURE 9B

MALKRINKELSDLARDPPAQCSAGPVGDDMFHWQATIMGPNDSPYQGGVFFLTIHFPTDYPFKPPKVAFTTRIYHPNINS
NGSICLDILRSQWSPALTISKVLLSICSLLCDPNPDDPLVPEIARIYKTDRDKYNRISREWTQKYAMZ

FIGURE 10

MKVKIKCWNGVATWLWVANDENCGICRMAFNGCCPDCKVPGDDCPLVWGQCSHCFHMHCILKWLHAQQVQQHCPMCRQTW
KFKE

FIGURE 11

MAAAMDVDTPSGTNSGAGKKRFEVKKWNAVALWAWDIVVDNCAICRNHIMDLCIECQANQASATSEECTVAWGVCNHAFHF
HCISRWLKTRQVCPLDNREWEFQKYGH

FIGURE 12A

ATGGCCGACGTGGAAGACGGAGAGGAAACCTGCGCCCTGGCCTCTCACTCCGGGAGCTCAGGCTCAACGTCGGGAGGCGA
CAAGATGTTCTCCCTCAAGAAGTGGAACCcGGTGGCCATGTGGAGCTGGGACGTGGAGTGCGATACGTGCGCCATCTGCA
GGGTCCAGGTGATGGATGCCTGTCTTAGATGTCAAGCTGAAAACAAACAAGAGGACTGTGTTGTGGTCTGGGGAGAATGT
AATCATTCCTTCCACAACTGCTGCATGTCCCTGTGGGTGAAACAGAACAATCGCTGCCCTCTCTGCCAGCAGGACTGGGT
GGTCCAAAGAATCGGCAAATGA

FIGURE 12B

MADVEDGEETCALASHSGSSGSTSGGDKMFSLKKWNPVAMWSWDVECDTCAICRVQVMDACLRCQAENKQEDCVVVWGEC
NHSFHNCCMSLWVKQNNRCPLCQQDWVVQRIGK

FIGURE 13A

```
ATGGCGACGTCTAATCTGTTAAAGAATAAAGGTTCTCTTCAGTTTGAAGACAAATGGGATTTTATGCGCCCGATTGTTTT
GAAGCTTTTACGCCAGGAATCTGTTACAAAACAGCAGTGGTTTGATCTGTTTTCGGATGTGCATGCAGTCTGTCTTTGGG
ATGATAAAGGCCCAGCAAAAATTCATCAGGCTTTAAAAGAAGATATTCTTGAGTTTATTAAGCAGGCACAGGCACGAGTA
CTGAGCCATCAAGATGATACGGCTTTGCTAAAAGCATATATTGTTGAATGGCGAAAGTTCTTTACACAATGTGATATTTT
ACCAAAACCTTTTTGTCAACTAGAGATTACTTTAATGGGTAAACAGGGCAGCAATAAAAAATCAAATGTGGAAGACAGTA
TTGTTCGAAAGCTTATGCTTGATACATGGAATGAGTCAATCTTTTCAAACATAAAAAACAGACTCCAAGATAGTGCAATG
AAGCTGGTACATGCTGAGAGATTGGGAGAAGCTTTTGATTCTCAGCTGGTTATTGGAGTAAGAGAATCCTATGTTAACCT
TTGTTCTAATCCTGAGGATAAACTTCAAATTTATAGGGACAATTTTGAGAAGGCATACTTGGATTCAACAGAGAGATTTT
ATAGAACACAAGCACCCTCGTATTTACAACCAAATGGTGTACAGAATTATATGAAATATGCAGATGCTAAATTAAAAGAA
GAAGAAAAACGAGCACTACGTTATTTAGAAACAAGACGAGAATGTAACTCCGTTGAAGCACTCATGGAATGCTGTGTAAA
TGCCCTGGTGACATCATTTAAAGAGACTATCTTAGCTGAGTGCCAAGGCATGATCAAGAGAAATGAAACTGAAAATTAC
ATTTAATGTTTTCATTGATGGACAAAGTTCCTAATGGTATAGAGCCAATGTTGAAAGACTTGGAGGAACATATCATTAGT
GCTGGCCTGGCAGATATGGTAGCAGCTGCTGAAACTATTACTACTGACTCTGAGAAATACGTTGAGCAGTTACTTACACT
ATTTAATAGATTTAGTAAACTCGTCAAAGAAGCTTTTCAAGATGATCCACGATTTCTTACTGCAAGAGATAAGGCGTATA
AAGCAGTTGTTAATGATGCTACCATATTTAAACTTGAACTTCCTTTGAAGCAGAAGGGGTGGATTAAAAACTCAGCCT
GAATCAAAATGCCCTGAGCTGCTTGCCAATTACTGTGACATGTTGCTAAGAAAAACACCATTAAGCAAAAAACTAACCTC
TGAAGAGATTGAAGCAAAGCTTAAAGAAGTGCTCTTGGTACTTAAGTATGTACAGAACAAAGATGTTTTTATGAGGTATC
ATAAAGCTCATTTGACACGACGTCTTATATTAGACATCTCTGCCGATAGTGAAATTGAAGAAAACATGGTAGAGTGGCTA
AGAGAAGTTGGTATGCCAGCGGATTATGTAAACAAGCTTGCTAGAATGTTTCAGGACATAAAAGTATCTGAAGATTTGAA
CCAAGCTTTTAAGGAAATGCACAAAAATAATAAATTGGCATTACCAGCTGATTCAGTTAATATAAAAATTCTGAATGCTG
GCGCCTGGTCAAGAAGTTCTGAGAAAGTCTTTGTCTCACTTCCTACTGAACTGGAGGACTTGATACCGGAAGTAGAAGAA
TTCTACAAAAAAAATCATAGTGGTAGAAAATTACATTGGCATCATCTCATGTCAAATGGAATTATAACATTTAAGAATGA
AGTTGGTCAATATGATTTGGAGGTAACCACGTTTCAGCTCGCTGTTTGTTTGCATGGAACCAAAGACCCAGAGAGAAAA
TCAGCTTTGAAAATCTTAAGCTTGCAACTGAACTCCCTGATGCTGAACTTAGGAGGACTTTATGGTCTTTAGTAGCTTTC
CCAAAACTCAAACGGCAAGTTTTTTTGTATGACCCTCAAGTCAACTCACCCAAAGACTTTACAGAAGGTACCCTCTTCTC
AGTGAACCAGGAGTTCAGTTTAATAAAAAATGCAAAGGTTCAGAAAAGGGGTAAAATCAACTTGATTGGACGTTTGCAGC
TCACTACAGAAGGATGAGAGAAGAAGAGAATGAAGGAATAGTTCAACTACGAATACTAAGAACCCAGGAAGCTATCATA
CAAATAATGAAAATGAGAAAGAAAATTAGTAATGCTCAGCTGCAGACTGAATTAGTAGAAATTTTGAAAAACATGTTCTT
GCCACAAAAGAAAATGATAAAAGAGCAAATAGAGTGGCTAATAGAGCACAAATACATCAGAAGAGATGAATCTGATATCA
ACACTTTCATATATATGGCATAA
```

FIGURE 13B

```
MRSFAWGSSGDHVGDKSEEAPGAWDEVSAVGALLQRPPHPGAGPTGPGPWWELRPPVKAWPGRERHEFSRRLVSRESKLK
NMATSNLLKNKGSLQFEDKWDFMRPIVLKLLRQESVTKQQWFDLFSDVHAVCLWDDKGPAKIHQALKEDILEFIKQAQAR
VLSHQDDTALLKAYIVEWRKFFTQCDILPKPFCQLEITLMGKQGSNKKSNVEDSIVRKLMLDTWNESIFSNIKNRLQDSA
MKLVHAERLGEAFDSQLVIGVRESYVNLCSNPEDKLQIYRDNFEKAYLDSTERFYRTQAPSYLQPNGVQNYMKYADAKLK
EEEKRALRYLETRRECNSVEALMECCVNALVTSFKETILAECQGMIKRNETEKLHLMFSLMDKVPNGIEPMLKDLEEHII
SAGLADMVAAAETITTDSEKYVEQLLTLFNRFSKLVKEAFQDDPRFLTARDKAYKAVVNDATIFKLELPLKQKGVGLKTQ
PESKCPELLANYCDMLLRKTPLSKKLTSEEIEAKLKEVLLVLKYVQNKDVFMRYHKAHLTRRLILDISADSEIEENMVEW
LREVGMPADYVNKLARMFQDIKVSEDLNQAFKEMHKNNKLALPADSVNIKILNAGAWSRSSEKVFVSLPTELEDLIPEVE
EFYKKNHSGRKLHWHHLMSNGIITFKNEVGQYDLEVTTFQLAVLFAWNQRPREKISFENLKLATELPDAELRRTLWSLVA
FPKLKRQVFLYDPQVNSPKDFTEGTLFSVNQEFSLIKNAVQKRGKINLIGRLQLTTERMREEENEGIVQLRILRTQEAI
IQIMKMRKKISNAQLQTELVEILKNMFLPQKKMIKEQIEWLIEHKYIRRDESDINTFIYMA
```

FIGURE 14A

```
atggcggcggcagttgtggtggcggaggggacagcgactcccggcccggacaggagttgttagtggcctggaacaccgt
gagcaccggcctggtgccgccggctgcgctggggctggtgtcttcccggaccagcggtgcagtcccgccaaaggaagagg
agctccgggcggcggtggaggttctgaggggccacgggctacactcggtcctggaggagtggttcgtggaggtgctgcag
aacgatctgcaggccaacatctcccctgagttctggaatgccatctcccaatgcgagaactctgcggatgagcccagtg
ccttttgctactccttgacgcttttggcctgctggagagccgcctggatccctacctgcgtagcctagagctgctggaga
atggactcgcctgggcttgctgatgggcactggtgctcaggggctgcgagaagaagtccacactatgttgcgcggagtc
ttgttctttagcaccccagaaccttccaagagatgatccagcgtctgtatgggtgcttcttgagagtctatatgcagag
taagaggaaggggaaggggcacagacccggaactggaagggagctggacagccggtatgcccgtcgccggtactacc
ggctcctgcagagcccgctgtgtgcagggtgcagcagtgacaagcaacagtgctggtgtcgccaggctctggagcagttc
catcagctcagccaggtcttacacaggctcagtctgctggagcgggtcagtgccgaggctgtgaccaccaccctgcacca
ggtgacccgggagaggatggaggaccgttgccggggcgagtacgagcgctccttcctgcgtgagttccacaagtggatcg
agcgggtggtcggctggctcggcaaggtgttcctgcaggacggccccgccaggcccgcatctcccgaggccggcaacacc
ctgcgccgctggcgctgccacgtgcaaaggttcttctaccgcatctacgccagcctgcgcatcgaggagctcttcagcat
cgtccgagacttcccagactcccggccagccatcgaggacctcaagtactgcctggagaggacggaccagaggcagcagc
tgctcgtgtccctcaaggctgccctggagactcggctcctgcatccaggcgtcaacacgtgtgacatcatcaccctctat
atctctgccatcaaggcgctgcgcgtgctggaccctccatggtcatcctggaggtggcctgtgagcctatccgccgcta
cctgaggacgcgggaggacacagtgcgcagattgtgcctgggctgacggggactcggacgggacaggggacctggctg
ttgagctgtccaagaccgacccggcgagcctggagacaggccaggacagtgaggatgactcaggcgagccagaggactgg
gtcccggaccctgtggatgccgatccagggaagtcgagctccaagcggcgttcatcggacatcatcagcctgctggtcag
catctacggcagcaaggacctcttcatcaatgagtaccgctcgctgctggccgaccgcctgctgcaccagttcagcttca
gccccgagcgggagatccgcaacgtggagctgctgaagctgcgctttggcgaggccccaatgcacttctgtgaagtcatg
ctgaaggacatggcggactcccgccgcatcaatgccaacatccgggaggaggatgagaagcggccagcagaggagcagcc
accgttcgggtctacgctgtcatcctgtccagtgagttctggccgcccttcaaggacgagaagctggaggtccccgagg
atatcagggcagccctggaggcttactgcaagaagtatgagcagctcaaggccatgcggacccctcagttggaagcacacc
ctgggcctggtgaccatggacgtggagctggccgaccgcacgctgtctgtggcggtcacccagtacaggcggtgatctt
gctgtattttcaggaccaagccagctggaccctggaggaactgagcaaggcggtgaaaatgccgtggcgctgctgcggc
ggcggatgtccgtgtggctgcagcagggtgtgctgcgtgaggagccccccggcaccttctctgtcattgaggaggagcgg
cctcaggaccgggacaacatggtgctcattgacagtgacgacgagagcgactccggcatggcctcccaggccgaccagaa
ggaggaggagctgctgctcttctggacgtacatccaggccatgctgaccaacctggagagcctctcactggatcgtatct
acaacatgctccgcatgtttgtggtgactgggcctgcactggccgagattgacctgcaggagctgcagggctacctgcag
aagaaggtgcgggaccagcagctcgtctactcggccggcgtctaccgcctgcccaagaactgcagctga
```

FIGURE 14B

```
MAAAVVVAEGDSDSRPGQELLVAWNTVSTGLVPPAALGLVSSRTSGAVPPKEEELRAAVEVLRGHGLHSVLEEWFVEVLQ
NDLQANISPEFWNAISQCENSADEPQCLLLLLDAFGLLESRLDPYLRSLELLEKWTRLGLLMGTGAQGLREEVHTMLRGV
LFFSTPRTFQEMIQRLYGCFLRVYMQSKRKGEGGTDPELEGELDSRYARRRYYRLLQSPLCAGCSSDKQQCWCRQALEQF
HQLSQVLHRLSLLERVSAEAVTTTLHQVTRERMEDRCRGEYERSFLREFHKWIERVVGWLGKVFLQDGPARPASPEAGNT
LRRWRCHVQRFFYRIYASLRIEELFSIVRDFPDSRPAIEDLKYCLERTDQRQQLLVSLKAALETRLLHPGVNTCDIITLY
ISAIKALRVLDPSMVILEVACEPIRRYLRTREDTVRQIVAGLTGDSDGTGDLAVELSKTDPASLETGQDSEDDSGEPEDW
VPDPVDADPGKSSSKRRSSDIISLLVSIYGSKDLFINEYRSLLADRLLHQFSFSPEREIRNVELLKLRFGEAPMHFCEVM
LKDMADSRRINANIREEDEKRPAEEQPPFGVYAVILSSEFWPPFKDEKLEVPEDIRAALEAYCKKYEQLKAMRTLSWKHT
LGLVTMDVELADRTLSVAVTPVQAVILLYFQDQASWTLEELSKAVKMPVALLRRRMSVWLQQGVLREEPPGTFSVIEEER
PQDRDNMVLIDSDDESDSGMASQADQKEEELLLFWTYIQAMLTNLESLSLDRIYNMLRMFVVTGPALAEIDLQELQGYLQ
KKVRDQQLVYSAGVYRLPKNCS
```

UBIQUITIN LIGASE ASSAY

FIELD OF THE INVENTION

This invention is directed to assays for measuring the activity of ubitquitination enzymes. The invention is also directed to assays for identifying modulators of ubiquitination.

BACKGROUND OF THE INVENTION

Ubiquitin is a highly conserved 76 amino acid protein expressed in all eukaryotic cells. The levels of many intracellular proteins are regulated by a ubiquitin-dependent proteolytic process. This process involves the covalent ligation of ubiquitin to a target protein, resulting in a polyubiquitinated target protein which is rapidly detected and degraded by the 26S proteasome.

The ubiquitination of these proteins is mediated by a cascade of enzymatic activity. Ubiquitin is first activated in an ATP-dependent manner by a ubiquitin activating enzyme (E1). The C-terminus of a ubiquitin forms a high energy thiolester bond with E 1. The ubiquitin is then passed to a ubiquitin conjugating enzyme (E2; also called ubiquitin carrier protein), also linked to this second enzyme via a thiolester bond. The ubiquitin is finally linked to its target protein to form a terminal isopeptide bond under the guidance of a ubiquitin ligase (E3). In this process, chains of ubiquitin are formed on the target protein, each covalently ligated to the next through the activity of E3.

The components of the ubiquitin ligation cascade have received considerable attention. E1 and E2 are structurally related and well characterized enzymes. There are several species of E2, some of which act in preferred pairs with specific E3 enzymes to confer specificity for different target proteins. E3 enzymes contain two separate activities: a ubiquitin ligase different target proteins. E3 enzymes contain two separate activities: a ubiquitin ligase activity to conjugate ubiquitin to substrates and form polyubiquitin chains via isopeptide bonds, and a targeting activity to physically bring the ligase and substrate together. Substrate specificity of different E3 enzymes is the major determinant in the selectivity of the ubiquitin-dependent protein degradation process.

E3 ligases that have been characterized include the HECT (homologous to E6-AP carboxy terminus) domain proteins, represented by the mammalian E6AP-E6 complex which functions as a ubiquitin ligase for the tumor suppressor p53 and which is activated by papillomavirus in cervical cancer (Huang et al., *Science* 286:1321–26 (1999)). The best characterized E3 ligase is the APC (anaphase promoting complex), which is a multi-subunit complex that is required for both entry into anaphase as well as exit from mitosis (see King et al., *Science* 274:1652–59 (1996) for review). The APC plays a crucial role in regulating the passage of cells through anaphase by promoting ubiquitin-dependent proteolysis of many proteins. In addition to degrading the mitotic B-type cyclin for inactivation of CDC2 kinase activity, the APC is also required for degradation of other proteins for sister chromatid separation and spindle disassembly. Most proteins known to be degraded by the APC contain a conserved nine amino acid motif known as the "destruction box" that targets them for ubiquitination and subsequent degradation. However, proteins that are degraded during G1, including G1 cyclins, CDK inhibitors, transcription factors and signaling intermediates, do not contain this conserved amino acid motif. Instead, substrate phosphorylation appears to play an important role in targeting their interaction with an E3 ligase for ubiquitination (see Hershko et al., *Ann. Rev. Biochem.* 67:429–75 (1998)).

In eukaryotes, a family of complexes with E3 ligase activity play an important role in regulating G1 progression. These complexes, called SCF's, consist of at least three subunits, SKP 1, Cullins (having at least seven family members) and an F-box protein (of which hundreds of species are known) which bind directly to and recruit the substrate to the E3 complex. The combinatorial interactions between the SCF's and a recently discovered family of RING finger proteins, the ROC/APC11 proteins, have been shown to be the key elements conferring ligase activity to E3 protein complexes. Particular ROC/Cullin combinations can regulate specific cellular pathways, as exemplified by the function of APC 11-APC2, involved in the proteolytic control of sister chromatid separation and exit from telophase into G1 in mitosis (see King et al., supra; Koepp et al., *Cell* 97:431–34 (1999)), and ROC1-Cullin 1, involved in the proteolytic degradation of $I_\kappa B_\alpha$ in $NF\text{-}_\kappa B/I_\kappa B$ mediated transcription regulation (Tan et al., *Mol. Cell* 3(4):527–533 (1999); Laney et al., *Cell* 97:427–30 (1999)).

Because the E3 complex is the major determinant of selection for protein degradation by the ubiquitin-dependent proteolytic process, modulators of E3 ligase activity may be used to upregulate or downregulate specific molecules involved in cellular signal transduction. Disease processes can be treated by such up- or down regulation of signal transducers to enhance or dampen specific cellular responses. This principle has been used in the design of a number of therapeutics, including Phosphodiesterase inhibitors for airway disease and vascular insufficiency, Kinase inhibitors for malignant transformation and Proteasome inhibitors for inflammatory conditions such as arthritis.

Due to the importance of ubiquitination in cellular regulation and the wide array of different possible components in ubiquitin-dependent proteolysis, there is a need for a fast and simple means for assaying E3 ligase activity. Furthermore, such an assay would be very useful for the identification of modulators of E3 ligase. Accordingly, it is an object of the present invention to provide methods of assaying ubiquitin ligase activity, which methods may further be used to identify modulators of ubiquitin ligase activity.

DESCRIPTION OF THE RELATED ART

Tan et al., supra, disclose that ROC1/Cullin catalyzes ubiquitin polymerization in the absence of target protein substrate. Ohta et al., *Mol. Cell* 3(4):535–541 (1999) disclose that APC11/APC2 also catalyze ubiquitin polymerization in the absence of target protein substrate, and that this activity is dependent on the inclusion of the proper E2 species. Rolfe et al., U.S. Pat. No. 5,968,761 disclose an assay for identifying inhibitors of ubiquitination of a target regulatory protein.

BRIEF DESCRIPTION OF THE DRAWINGS

FIG. 3 shows relative ubiquitin ligase activity in an assay combining ubiquitin, E1, E2 and E3.

FIG. 5 shows the concentration-dependent effect of two ubiquitin ligase activity modulators in assays measuring ubiquitin ligase activity with two different E3 enzymes.

FIG. 6 shows the proportions of ubiquitin ligase activity and ubiquitin conjugating activity in the presence and absence of two candidate ubiquitin ligase enzyme modulators for combinations of E1, E2 and E3 and combinations of enzymes E1 and E2.

FIG. 7 shows the concentration-dependent effects of two candidate ubiquitin ligase modulators on ubiquitin ligase activity and ubiquitin conjugating activity.

FIGS. 8A and 8B (SEQ ID NOS:1–2) show the nucleic acid sequence encoding rabbit E1 and the amino acid sequence of rabbit E1, respectively.

FIGS. 9A and 9B (SEQ ID NOS:3–4) show the nucleic acid sequence encoding the E2 Ubc5c and the amino acid sequence of the E2 Ubc5c, respectively.

FIG. 10 (SEQ ID NO:5) shows the amino acid sequence of the RING finger protein APC11.

FIG. 11 (SEQ ID NO:6) shows the amino acid sequence of the RING finger protein ROC1.

FIGS. 12A and 12B (SEQ ID NOS:7–8) show the nucleic acid sequence encoding the RING finger protein ROC2 and the amino acid sequence of ROC2, respectively.

FIGS. 13A and 13B (SEQ ID NOS:9–10) show the nucleic acid sequence encoding the Cullin CUL5 and the amino acid sequence of CUL5, respectively.

FIGS. 14A and 14B (SEQ ID NOS:11–12) show the nucleic acid sequence encoding the Cullin APC2 and the amino acid sequence of APC2, respectively.

DETAILED DESCRIPTION OF THE INVENTION

Figure 1:
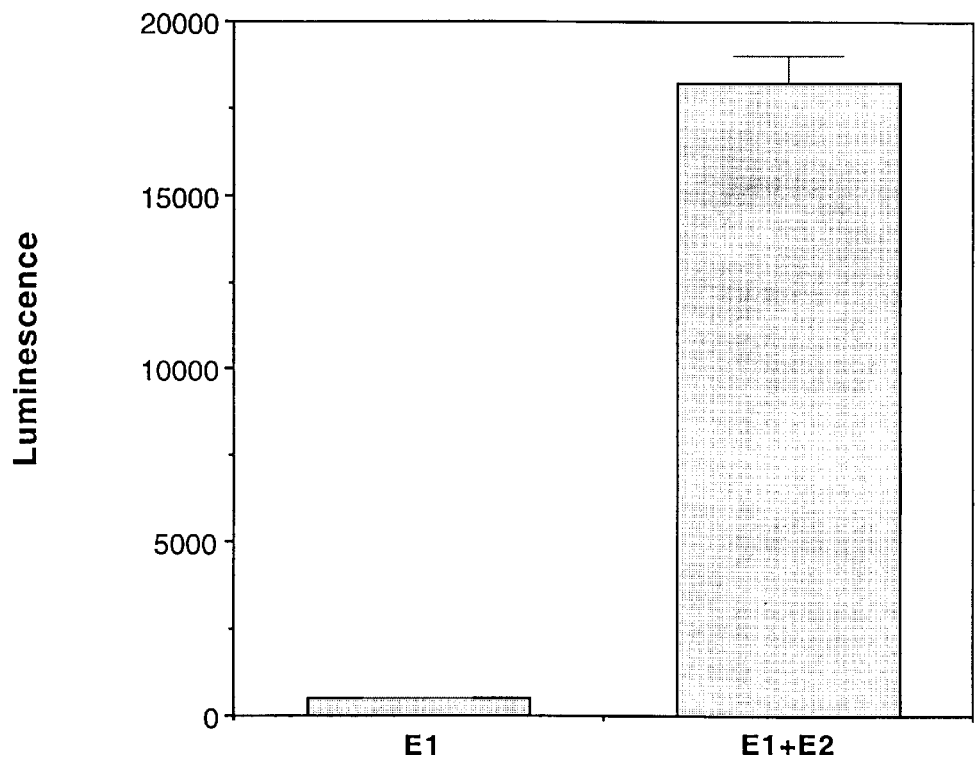
FIG. 1 shows the relative amounts of fluorescently labeled ubiquitin in a ubiquitin activating and conjugating assay. In these experiments, E2 is His-Ubch5c.

The present invention is directed to methods for assaying ubiquitin ligase activity. In a broad embodiment, the method provides measuring ubiquitin ligase activity directly where the reaction has occurred, thus obviating the need for target proteins and subsequent analysis such as separating ligated material in an SDS PAGE procedure. This thus allows multi-well array analysis and high throughput screening techniques for modulators of ligase activity. In addition, the present methods allow the use of many different combinations of E3 components and E2/E3 combinations, without requiring prior identification of specific target substrates.

In general, the method involves combining ubiquitin and ubiquitin ligation enzymes and measuring the amount of ubiquitin ligated to a ubiquitination substrate protein. In a preferred embodiment, the ubiquitination substrate protein is ubiquitin itself, therefore what is measured is poly-ubiquitin chains produced in the ligase reaction.

In a preferred embodiment, no specific target protein is used to measure ubiquitin ligase activity. By "target protein" herein is meant a protein other than ubiquitin to which ubiquitin is ligated by ubiquitination enzymes. In this embodiment, preferably, the poly-ubiquitin chains measured are bound to E3.

In a preferred embodiment, E3 is attached to the surface of a reaction vessel, such as the well of a multi-well plate. This embodiment facilitates the separation of ligated ubiquitin from unligated ubiquitin. Means of attaching E3 to the surface of a reaction vessel are described below. This embodiment allows the ubiquitin ligase reaction and detection and measurement of ligated ubiquitin to occur in the same vessel, making the assay useful for high-throughput screening applications.

In a preferred embodiment, the ubiquitin is labeled, either directly or indirectly, as further described below, and the amount of label is measured. This allows for easy and rapid detection and measurement of ligated ubiquitin, making the assay useful for high-throughput screening applications. One of ordinary skill in the art will recognize the applicability of the present invention to screening for agents which modulate ubiquitination enzyme activity.

Accordingly, the present invention provides methods and compositions for assaying ubiquitin ligase activity. By "ubiquitin" herein is meant a polypeptide which is ligated to another polypeptide by ubiquitin ligase enzymes. The ubiquitin can be from any species of organism, preferably a eukaryotic species. Preferably, the ubiquitin is mammalian. More preferably, the ubiquitin is human ubiquitin.

In a preferred embodiment, when ubiquitin is ligated to a target protein, that protein is targeted for degradation by the 26S proteasome.

Preferred embodiments of the invention utilize a 76 amino acid human ubiquitin. Other embodiments utilize variants of ubiquitin, as further described below.

Also encompassed by "ubiquitin" is naturally occurring alleles and man-made variants of such a 76 amino acid polypeptide. In a preferred embodiment, the ubiquitin has the amino acid sequence of amino acids 1–76 of ATCC accession number AAA36789 or AAB06013, incorporated herein by reference. In a preferred embodiment, variants of ubiquitin have an overall amino acid sequence identity of preferably greater than about 75%, more preferably greater than about 80%, even more preferably greater than about 85% and most preferably greater than 90% of the amino acid sequence of amino acids 1–76 of ATCC accession number AAA36789 or AAB06013. In some embodiments the sequence identity will be as high as about 93 to 95 or 98%.

In another preferred embodiment, a ubiquitin protein has an overall sequence similarity with the amino acid sequence of amino acids 1–76 of ATCC accession number AAA36789 or AAB06013 of greater than about 80%, more preferably greater than about 85%, even more preferably greater than about 90% and most preferably greater than 93%. In some embodiments the sequence identity will be as high as about 95 to 98 or 99%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., *Methods in Enzymology*, 266: 460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the amino acid sequence of amino acids 1–76 of ATCC accession number AAA36789 or AABO6013, it is understood that in one embodiment, the percentage of sequence identity will be determined based on the number of identical amino acids in relation to the total number of amino acids. Thus, for example, sequence identity of sequences shorter than that of amino acids 1–76 of ATCC accession number AAA36789 or AAB06013, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Ubiquitin proteins of the present invention may be shorter or longer than the amino acid sequence of amino acids 1–76 of ATCC accession number AAA36789 or AAB06013. Thus, in a preferred embodiment, included within the definition of ubiquitin are portions or fragments of the amino acid sequence of amino acids 1–76 of ATCC accession number AAA36789 or AAB06013. In one embodiment herein, fragments of ubiquitin are considered ubiquitin proteins if they are ligated to another polypeptide by ubiquitin ligase enzymes.

In addition, as is more fully outlined below, ubiquitin can be made longer than that depicted in the amino acid sequence of amino acids 1–76 of ATCC accession number AAA36789 or AAB06013; for example, by the addition of tags, the addition of other fusion sequences, or the elucidation of additional coding and non-coding sequences. As described below, the fusion of a ubiquitin peptide to a fluorescent peptide, such as Green Fluorescent Peptide (GFP), is particularly preferred.

The ubiquitin protein, as well as other proteins of the present invention, are preferably recombinant. A "recombinant protein" is a protein made using recombinant techniques, i.e. through the expression of a recombinant nucleic acid as described below. In a preferred embodiment, the ubiquitin of the invention is made through the expression of the nucleic acid of ATCC accession number M26880 or U49869, or fragment thereof. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in the figures also include the complement of the sequence. By the term "recombinant nucleic acid" herein is meant nucleic acid, originally formed in vitro, in general, by the manipulation of nucleic acid by endonucleases, in a form not normally found in nature. Thus an isolated nucleic acid, in alinear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

The terms "polypeptide" and "protein" may be used interchangeably throughout this application and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

In one embodiment, the present invention provides compositions containing protein variants, for example ubiquitin, E1, E2 and/or E3 variants. These variants fall into one or more of three classes: substitutional, insertional or deletional variants. These variants ordinarily are prepared by site specific mutagenesis of nucleotides in the DNA encoding a protein of the present compositions, using cassette or PCR mutagenesis or other techniques well known in the art, to produce DNA encoding the variant, and thereafter expressing the DNA in recombinant cell culture as outlined above. However, variant protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal desired activity. Techniques for making substitution mutations at predetermined sites in DNA having a known sequence are well known, for example, M13 primer mutagenesis and PCR mutagenesis. Rapid production of many variants may be done using techniques such as the method of gene shuffling, whereby fragments of similar variants of a nucleotide sequence are allowed to recombine to produce new variant combinations. Examples of such techniques are found in U.S. Pat. Nos. 5,605,703; 5,811,238; 5,873,458; 5,830,696; 5,939,250; 5,763,239; 5,965,408; and 5,945,325, each of which is incorporated by reference herein in its entirety. Screening of the mutants is done using ubiquitin ligase activity assays of the present invention.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the protein are desired, substitutions are generally made in accordance with the following chart:

CHART 1

| Original Residue | Exemplary Substitutions |
| --- | --- |
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the proteins as needed. Alternatively, the variant may be designed such that the biological activity of the protein is altered. For example, glycosylation sites may be altered or removed.

Covalent modifications of polypeptides are included within the scope of this invention. One type of covalent modification includes reacting targeted amino acid residues of a polypeptide with an organic derivatizing agent that is capable of reacting with selected side chains or the N-or C-terminal residues of a polypeptide. Derivatization with bifunctional agents is useful, for instance, for crosslinking a protein to a water-insoluble support matrix or surface for use in the method for screening assays, as is more fully described below. Commonly used crosslinking agents include, e.g., 1,1-bis(diazoacetyl)-2-phenylethane, glutaraldehyde, -hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of a polypeptide included within the scope of this invention comprises altering the native glycosylation pattern of the polypeptide. "Altering the native glycosylation pattern" is intended for purposes herein to mean deleting one or more carbohydrate moieties found in native sequence polypeptide, and/or adding one or more glycosylation sites that are not present in the native sequence polypeptide.

Addition of glycosylation sites to polypeptides may be accomplished by altering the amino acid sequence thereof. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on a polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of a protein comprises linking the polypeptide to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Polypeptides of the present invention may also be modified in a way to form chimeric molecules comprising a first polypeptide fused to another, heterologous polypeptide or amino acid sequence. In one embodiment, such a chimeric molecule comprises a fusion of a ubiquitin polypeptide (or an E2 or an E3, as defined below) with a tag polypeptide which provides an epitope to which an anti-tag antibody can selectively bind. The epitope tag is generally placed at the amino-or carboxyl-terminus of the polypeptide. The presence of such epitope-tagged forms of a polypeptide can be detected using an antibody against the tag polypeptide. Also, provision of the epitope tag enables the polypeptide to be readily purified by affinity purification using an anti-tag antibody or another type of affinity matrix that binds to the epitope tag. In an alternative embodiment, the chimeric molecule may comprise a fusion of a polypeptide disclosed herein with an immunoglobulin or a particular region of an immunoglobulin. For a bivalent form of the chimeric molecule, such a fusion could be to the Fc region of an IgG molecule. Tags for components of the invention are defined and described in detail below.

The present invention provides methods for assaying ubiquitin ligase activity. By "ubiquitin ligase" is meant a ubiquitination enzyme capable of catalyzing the covalent binding of a ubiquitin to another protein. Preferred embodiments of the invention involve combining ubiquitin and ubiquitination enzymes, including ubiquitin ligase, and measuring the amount of ubiquitin (poly-ubiquitin) bound to the ubiquitin ligase. In a preferred embodiment, the ubiquitin ligase is an E3 ubiquitin ligase, defined below.

Embodiments of the present invention involve binding ubiquitin to a ubiquitination substrate protein. By "ubiquitination substrate protein" is meant a protein to which the ubiquitin ligase can catalyze the covalent binding of ubiquitin and includes target proteins and ubiquitin. In a preferred embodiment, the ubiquitination substrate protein is ubiquitin and the ubiquitin ligase catalyzes the formation of polyubiquitin chains. Preferably, the polyubiquitin chains are formed by the ubiquitin ligase in the absence of any target protein.

In a preferred embodiment, the invention is directed to a method of assaying ubiquitin ligase activity. By "ubiquitin ligase activity", "ubiquitin ligation" and grammatical equivalents thereof is meant the catalysis of the covalent binding of ubiquitin to a substrate protein. Preferably, each ubiquitin is bound such that a subsequent ubiquitin polypeptide may be bound to it, to form chains comprising a plurality of ubiquitin molecules. In a preferred embodiment, ubiquitin ligase activity occurs in the absence of target proteins.

In a preferred embodiment, the invention is additionally directed to a method of assaying ubiquitin activating activity. By "ubiquitin activating activity", "ubiquitin activation" and grammatical equivalents thereof is meant the binding of ubiquitin and E1. Preferably, E1 forms a high energy thiolester bond with the ubiquitin.

In a preferred embodiment, the invention is also directed to a method of assaying ubiquitin conjugating activity. By "ubiquitin conjugating activity", "ubiquitin conjugation" and grammatical equivalents thereof is meant the binding of activated ubiquitin with E2. As will 30 be appreciated by those in the art, due to the presence of the high energy thiolester bond in the E2-ubiquitin conjugate, conjugated ubiquitin may be joined to other ubiquitin at a low rate in the absence of the catalytic activity of E3. Therefore, some of the ubiquitin measured in a ubiquitin conjugating activity assay will be in the form of poly-ubiquitin.

The present invention provides methods and compositions comprising combining ubiquitin with other components. By "combining" is meant the addition of the various components into a receptacle under conditions whereby ubiquitin ligase activity may take place. In a preferred embodiment, the receptacle is a well of a 96 well plate or other commercially available multiwell plate. In an alternate preferred embodiment, the receptacle is the reaction vessel of a FACS machine. Other receptacles useful in the present invention include, but are not limited to 384 well plates and 1536 well plates. Still other receptacles useful in the present invention will be apparent to the skilled artisan.

The addition of the components may be sequential or in a predetermined order or grouping, as long as the conditions amenable to ubiquitin ligase activity are obtained. Such conditions are well known in the art, and further guidance is provided below.

In a preferred embodiment, one or more components of the present invention comprise a tag. By "tag" is meant an attached molecule or molecules useful for the identification or isolation of the attached component. Components having a tag are referred to as "tag-X", wherein X is the component. For example, a ubiquitin comprising a tag is referred to herein as "tag-ubiquitin". Preferably, the tag is covalently bound to the attached component. When more than one component of a combination has a tag, the tags will be numbered for identification, for example "tag1-ubiquitin". Preferred tags include, but are not limited to, a label, a partner of a binding pair, and a surface substrate binding molecule. As will be evident to the skilled artisan, many molecules may find use as more than one type of tag, depending upon how the tag is used.

By "label" is meant a molecule that can be directly (i.e., a primary label) or indirectly (i.e., a secondary label) detected; for example a label can be visualized and/or measured or otherwise identified so that its presence or absence can be known. As will be appreciated by those in the art, the manner in which this is done will depend on the label. Preferred labels include, but are not limited to, fluorescent labels, label enzymes and radioisotopes.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., *Science* 263(5148):802–805 (Feb. 11, 1994); and EGFP; Clontech—Genbank Accession Number U55762 ), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462–471 (1998); 3. Heim, R. and Tsien, R. Y. Curr. Biol. 6:178–182 (1996)), enhanced yellow fluorescent protein (EYFP; 1. Clontech Laboratories, Inc., 1020 East Meadow Circle, Palo Alto, Calif. 94303), luciferase (Ichiki, et al., *J. Immunol.* 150(12):5408–5417 (1993)), β-galactosidase (Nolan, et al., *Proc Natl Acad Sci USA* 85(8):2603–2607 (April 1988)) and Renilla WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558) All of the above-cited references are expressly incorporated herein by reference.

By "label enzyme" is meant an enzyme which may be reacted in the presence of a label enzyme substrate which produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., *Previews* 247:6–9 (1998), Young, *J. Virol. Methods* 24:227–236 (1989), which are each hereby incorporated by reference in their entirety.

By "radioisotope" is meant any radioactive molecule. Suitable radioisotopes for use in the invention include, but are not limited to $^{14}$C, $^{3}$H, $^{32}$P, $^{33}$P, 35S, $^{125}$I, and $^{131}$I. The use of radioisotopes as labels is well known in the art.

In addition, labels may be indirectly detected, that is, the tag is a partner of a binding pair. By "partner of a binding pair" is meant one of a first and a second moiety, wherein said first and said second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avid (or biotin/streptavidin) and calmodulin binding protein (CBP)/calmodulin. Other suitable binding pairs include polypeptides such as FLAG (DYKDDDDK; SEQ ID NO:13) [Hopp et al., *BioTechnology*, 6:1204–1210 (1988)]; the KT3 epitope peptide [Martin et al., *Science*, 255:192–194 (1994)]; tubilin epitope peptide [skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)] and the antibodies each thereto. Generally, in a preferred embodiment, the smaller of the binding pair partners serves as the tag, as steric considerations in ubiquitin ligation may be important. As will be appreciated by those in the art, binding pair partners may be used in applications other than for labeling, as is further described below.

As will be appreciated by those in the art, a partner of one binding pair may also be a partner of another binding pair. For example, an antigen (first moiety) may bind to a first antibody (second moiety) which may, in turn, be an antigen to a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag which is a partner of a binding pair, as just described, is referred to herein as "indirect labeling".

By "surface substrate binding molecule" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate [Field et al., *Mol. Cell. Biol.*, 8:2159–2165 (1988)]; the c-myc tag and the 8F9, 3C7, 6E10, G4, B7 and 9E10 antibody substrates thereto [Evan et al., *Molecular and Cellular Biology*, 5:3610–3616 (1985)]; and the Herpes Simplex virus glycoprotein D (gD) tag and its antibody substrate [Paborsky et al., *Protein Engineering*, 3(6):547–553 (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of substrate-embedded antibodies is well known; see Slinkin et al., *Bioconj. Chem.* 2:342–348 (1991); Torchilin et al., supra; Trubetskoy et al., *Bioconj. Chem.* 3:323–327 (1992); King et al., *Cancer Res.* 54:6176–6185 (1994); and Wilbur et al., *Bioconjugate Chem.* 5:220–235 (1994) (all of which are hereby expressly incorporated by reference), and attachment of or production of proteins with antigens is described above.

Calmodulin-embedded substrates are commercially available, and production of proteins with CBP is described in Simcox et al., Strategies 8:40–43 (1995), which is hereby incorporated by reference in its entirety.

As will be appreciated by those in the art, tag-components of the invention can be made in various ways, depending largely upon the form of the tag. Components of the invention and tags are preferably attached by a covalent bond.

The production of tag-polypeptides by recombinant means when the tag is also a polypeptide is described below. Production of FLAG (DYKDDDDK; SEQ ID NO:13)-labeled proteins is well known in the art and kits for such production are commercially available (for example, from Kodak and Sigma). Methods for the production and use of FLAG (DYKDDDDK; SEQ ID NO:13)-labeled proteins are found, for example, in Winston et al., *Genes and Devel.* 13:270–283 (1999), incorporated herein in its entirety, as well as product handbooks provided with the above-mentioned kits.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known (Id.).

Methods for labeling of proteins with radioisotopes are known in the art. For example, such methods are found in Ohta et al., *Molec. Cell* 3:535–541 (1999), which is hereby incorporated by reference in its entirety.

Production of proteins having His-tags by recombinant means is well known, and kits for producing such proteins are commercially available. Such a kit and its use is described in the QIAexpress Handbook from Quiagen by Joanne Crowe et al., hereby expressly incorporated by reference.

The functionalization of labels with chemically reactive groups such as thiols, amines, carboxyls, etc. is generally known in the art. In a preferred embodiment, the tag is functionalized to facilitate covalent attachment.

The covalent attachment of the tag may be either direct or via a linker. In one embodiment, the linker is a relatively short coupling moiety, that is used to attach the molecules. A coupling moiety may be synthesized directly onto a component of the invention, ubiquitin for example, and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In a preferred embodiment, the covalent attachment is direct, that is, no linker is used. In this embodiment, the component preferably contains a functional group such as a carboxylic acid which is used for direct attachment to the functionalized tag. It should be understood that the component and tag may be attached in a variety of ways, including those listed above. What is important is that manner of attachment does not significantly alter the functionality of the component. For example, in tag-ubiquitin, the tag should be attached in such a manner as to allow the ubiquitin to be covalently bound to other ubiquitin to form polyubiquitin chains. As will be appreciated by those in the art, the above description of covalent attachment of a label and ubiquitin applies equally to the attachment of virtually any two molecules of the present disclosure.

In a preferred embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above or a component of the invention. Thus, for example, for direct linkage to a carboxylic acid group of a ubiquitin, amino modified or hydrazine modified tags will be used for coupling via carbodiimide chemistry, for example using 1-ethyl-3-(3-dimethylaminopropyl)-carbodiimide (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the tag, such as is commercially available for many of the tags described herein.

In a preferred embodiment, ubiquitin is in the form of tag-ubiquitin.

In a preferred embodiment, ubiquitin is in the form of tag-ubiquitin, wherein, tag is a partner of a binding pair. Preferably in this embodiment the tag is FLAG (DYKDDDDK; SEQ ID NO:13) and the binding partner is anti-FLAG (DYKDDDDK; SEQ ID NO:13). Preferably in this embodiment, a label is attached to FLAG (DYKDDDDK; SEQ ID NO:13) by indirect labeling. Preferably, the label is a label enzyme. Most preferably, the label enzyme is horseradish peroxidase, which is reacted with a fluorescent label enzyme substrate. Preferably, the label enzyme substrate is Luminol. Alternatively, the label is a fluorescent. label.

The present invention provides methods and compositions comprising combining ubiquitin and E1. By "E1" is meant a ubiquitin activating enzyme. In a preferred embodiment, E1 is capable of transferring ubiquitin to an E2, defined below. In a preferred embodiment, E1 binds ubiquitin. In a preferred embodiment, E1 forms a high energy thiolester bond with ubiquitin, thereby "activating" the ubiquitin.

In a preferred embodiment, E1 proteins useful in the invention include those having the amino acid sequence of the polypeptide having ATCC accession numbers A38564, S23770, AAA61246, P22314, CAA40296 and BAA33144, incorporated herein by reference. In a preferred embodiment, E1 has the amino acid sequence shown in FIG. 8B (SEQ ID NO:2) or is encoded by a nucleic acid comprising the sequence shown in FIG. 8A (SEQ ID NO:1). E1 is commercially available from Affiniti Research Products (Exeter, U.K.).

In a preferred embodiment, nucleic acids which may be used for producing E1 proteins for the invention include, but are not limited to, those disclosed by ATCC accession numbers M58028, X56976 and AB012190, incorporated herein by reference. In a preferred embodiment, E1 is encoded by a nucleic acid having a sequence consisting essentially of the sequence shown in FIG. 8A (SEQ ID NO:1). Variants of the cited E1 proteins, also included in the term "E1", can be made as described herein In a preferred embodiment, the compositions of the invention comprise E2. By "E2" is meant a ubiquitin carrier enzyme (also known as a ubiquitin conjugating enzyme). In a preferred embodiment, ubiquitin is transferred from E1 to E2. In a preferred embodiment, the transfer results in a thiolester bond formed between E2 and ubiquitin. In a preferred embodiment, E2 is capable of transferring ubiquitin to an E3, defined below. In a preferred embodiment, the ubiquitination substrate protein is ubiquitin.

In a preferred embodiment, proteins which may be used in the present invention as E2 include, but are not limited to, those having the amino acid sequences disclosed in ATCC accession numbers AAC37534, P49427, CAA82525, AAA58466, AAC41750, P51669, AAA91460, AAA91461, CAA63538, AAC50633, P27924, AAB36017, Q16763, AAB86433, AAC26141, CAA04156, BAA11675, Q16781 and CAB45853, each of which is incorporated herein by reference. In a preferred embodiment, E2 is Ubc5c. In a preferred embodiment, E2 has the amino acid sequence shown in FIG. 9B (SEQ ID NO:4) or is encoded by a nucleic acid consisting essentially of the sequence shown in FIG. 9A (SEQ ID NO:3). Also specifically included within the term "E2" are variants of E2, which can be made as described herein.

In a preferred embodiment, nucleic acids which may be used to make E2 include, but are not limited to, those nucleic acids having sequences disclosed in ATCC accession numbers L2205, Z29328, M92670, L40146, U39317, U39318, X92962, U58522, S81003, AF031141, AF075599, AJ000519, and D83004, each of which is incorporated herein by reference. In a preferred embodiment, the nucleic acid used to make E2 comprises the sequence shown in FIG. 9A (SEQ ID NO:3). As described above, variants of these and other E2 encoding, nucleic acids may also be used to make variant E2 proteins.

In a preferred embodiment, E2 has a tag, as defined above, with the complex being referred to herein as "tag-E2". Preferred E2 tags include, but are not limited to, labels, partners of binding pairs and substrate binding elements. In a most preferred embodiment, the tag is a His-tag or GST-tag.

The present invention provides methods and compositions comprising E3. By "E3" is meant a ubiquitin ligase, as defined above, comprising one or more components associated with ligation of ubiquitin to a ubiquitination substrate protein for ubiquitin-dependent proteolysis. In a preferred embodiment, E3 comprises a ring finger protein and a Cullin. In a preferred embodiment, RING finger proteins include, but are not limited to, ROC1, ROC2 and APC11. In a preferred embodiment, Cullins include, but are not limited to, CUL1, CUL2, CUL3, CUL4A, CUL4B, CUL5 and APC2.

In a preferred embodiment, RING finger proteins include, but are not limited to, proteins having the amino acid sequence disclosed in ATCC accession numbers AAD30147 and AAD30146 and 6320196, incorporated herein by reference. In a more preferred embodiment, the ring finger protein has a sequence selected from the group consisting of that shown in FIGS. 10, 11, and 12B (SEQ ID NOS:5, 6 and 8).

In a preferred embodiment, Cullins include, but are not limited to, proteins having the amino acid sequences disclosed in ATCC accession numbers 4503161, AAC50544, AAC36681, 4503163, AAC51190, AAD23581, 4503165, AAC36304, AAC36682, AAD45191, AAC50548, Q13620, 4503167 and AAF0575 1, each of which is incorporated herein by reference. In a preferred embodiment, the Cullin has a sequence as shown in FIG. 13B or 14B (SEQ ID NO:10 or 12). In addition, in the context of the invention, each of the RING finger proteins and Cullins encompass variants of the known or listed sequences, as described herein.

These E3 proteins and variants may be made as described herein. In a preferred embodiment, nucleic acids used to make the RING finger proteins include, but are not limited to, those having the nucleic acid sequences disclosed in ATCC accession numbers AF142059, AF142060 and nucleic acids 433493 to 433990 of NC 001136. In a preferred embodiment, Cullins are made from nucleic acids including, but not limited to, those having nucleic acid sequences disclosed in ATCC accession numbers NM 003592, U58087, AF062536, AF126404, NM 003591, U83410, NM 003590, AB014517, AF062537, AF064087, AF077188, U58091, NM 003478, X81882 and AF191337, each of which is incorporated herein by reference. As described above, variants of these sequences are also encompassed by the invention.

In an alternate embodiment, E3 comprises the ligase E3-alpha, E3A (E6-AP), HERC2, SMURF1 or NEDD-4. In this embodiment, the ligase has the amino acid sequence of that disclosed in ATCC accession number AAC39845, Q05086, CAA66655, CAA66654, CAA66656, AAD08657, AAF08298 or P46934, each of which is incorporated herein by reference. As above, variants are also encompassed by the invention. Nucleic acids for making E3 for this embodiment include, but are not limited to, those having the sequences disclosed in ATCC accession numbers AF061556, X898032, X9803 1, X98033, AF071172, AF199364 and D42055 and variants thereof.

E3 may also comprise other components, such as SKP1 and F-box proteins. The amino acid and nucleic acid sequences for SKP1 are found in ATCC accession numbers AAC50241 and U33760, respectively. Many F-box proteins are known in the art and their amino acid and nucleic acid sequences are readily obtained by the skilled artisan from various published sources.

In a preferred embodiment, the E3 components are produced recombinantly, as described herein.

In a preferred embodiment, the E3 components are co-expressed in the same host cell. Co-expression may be achieved by transforming the cell with a vector comprising nucleic acids encoding two or more of the E3 components, or by transforming the host cell with separate vectors, each comprising a single component of the desired E3 protein complex. In a preferred embodiment, the RING finger protein and Cullin are expressed in a single host transfected with two vectors, each comprising nucleic acid encoding one or the other polypeptide, as described in further detail in the Examples.

In a preferred embodiment, E3 has a tag, which complex is referred to herein as "tag-E3". Preferably, the tag is attached to only one component of the E3. Preferred E3 tags include, but are not limited to, labels, partners of binding pairs and substrate binding elements. More preferably, the tag is a surface substrate binding molecule. Most preferably, the tag is a His-tag or GST-tag.

In an embodiment herein, ubiquitin and ubiquitination enzymes and their components are cloned and expressed as outlined below. Thus, probe or degenerate polymerase chain reaction (PCR) primer sequences may be used to find other related ubiquitination proteins from humans or other organisms. As will be appreciated by those in the art, particularly useful probe and/or PCR primer sequences include the unique areas of a nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences cited herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant nucleic acid can be further-used as a probe to identify and isolate other nucleic acids. It can also be used as a "precursor" nucleic acid to make modified or variant nucleic acids and proteins.

Using the nucleic acids of the present invention which encode a protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading fram. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the protein; for example, transcriptional and translational regulatory nucleic acid sequences from Bacillus are preferably used to express the protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Proteins of the present invention are produced by culturing a host cell transformed with an expression vector containing nucleic acid encoding the protein, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melanogaster* cells, *Saccharomyces cerevisiae* and other yeasts, *E. coli, Bacillus subtilis*, SF9 cells, C129 cells, Saos-2 cells, Hi-5 cells, 293 cells, Neurospora, BHK, CHO, COS, and HeLa cells. Of greatest interest are *E. coli*, SF9 cells and Hi-5 cells.

In a preferred embodiment, the proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for a protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of a protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. Coli*, the ribosome binding site is called the Shine-Delgamo (SD) sequence and includes an initiation codon and a sequence 3–9 nucleotides in length located 3–11 nucleotides upstream of the initiation codon.

The expression vector may also include a signal peptide sequence that provides for secretion of the protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, proteins are produced in insect cells. Expression vectors for the transformation of insect cells, and in particular, baculovirus-based expression vectors, are well known in the art.

In a preferred embodiment, proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K lactis, Pichia guillerimondii* and *P. pastoris, Schizosaccharomyces pombe,* and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The protein may also be made as a fusion protein, using techniques well known in the art. Thus, for example, the protein may be made as a fusion protein to increase expression, or for other reasons. For example, when the protein is a peptide, the nucleic acid encoding the peptide may be linked to other nucleic acid for expression purposes. Similarly, proteins of the invention can be linked to protein labels, such as green fluorescent protein (GFP), red fluorescent protein (RFP), blue fluorescent protein (BFP), yellow fluorescent protein (YFP), etc.

In a preferred embodiment, the protein is purified or isolated after expression. Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the ubiquitin protein may be purified using a standard anti-ubiquitin antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the protein. In some instances no purification will be necessary.

Once made, the compositions find use in a number of applications, including, but not limited to, screens for modulators of ubiquitin ligase activity. By "modulator" is meant a compound which can increase or decrease ubiquitin ligase activity. By "candidate", "candidate agent", "candidate modulator", "candidate ubiquitin ligase activity modulator" or grammatical equivalents herein is meant any molecule, e.g. proteins (which herein includes proteins, polypeptides, and peptides), small organic or inorganic molecules, polysaccharides, polynucleotides, etc. which are to be tested for ubiquitin ligase activity modulator activity. Candidate agents encompass numerous chemical classes. In a preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate modulators are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In a preferred embodiment, candidate modulators are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate modulator prior to the assay; only candidate modulators that increase or decease ubiquitin ligase activity need be identified. In addition, as is known in the art, coding tags using split synthesis reactions may be done, to essentially identify the chemical moieties tested.

Alternatively, a preferred embodiment utilizes libraries of natural compounds in the form of bacterial, fungal, plant and animal extracts that are available or readily produced.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate modulators include proteins, nucleic acids, and chemical moieties.

In a preferred embodiment, the candidate modulator are proteins, as defined above. In a preferred embodiment, the candidate modulators are naturally occurring proteins or fragments of naturally occurring proteins. Thus, for example, cellular extracts containing proteins, or random or directed digests of proteinaceous cellular extracts, may be tested, as is more fully described below. In this way libraries of procaryotic and eucaryotic proteins may be made for screening against any number of ubiquitin ligase compositions. Particularly preferred in this embodiment are libraries of bacterial, fungal, viral, and mammalian proteins, with the latter being preferred, and human proteins being especially preferred.

In a preferred embodiment, the candidate modulators are peptides of from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow interaction with a particular ubiquitin ligase enzyme. Accordingly, an interaction library must be large enough so that at least one of its members will have a structure that interacts with a ubiquitin ligase enzyme. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for a target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate modulator is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumor and anti-microbial activity. Short peptide fragments of a protein kinase C isozyme (BPKC), have been shown to block nuclear translocation of BPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate modulators as well. Thus, a number of molecules or protein domains are suitable as starting points for the generation of biased randomized candidate modulators. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc.

In a preferred embodiment, the candidate modulators are nucleic acids. With reference to candidate modulators, by "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 1 10:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As described above generally for proteins, nucleic acid candidate modulator may be naturally occurring nucleic acids, random nucleic acids, or "biased" random nucleic acids. For example, digests of procaryotic or eucaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, the candidate modulators are organic moieties. In this embodiment, as is generally described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As will be appreciated by those in the art, it is possible to screen more than one type of candidate modulator at a time. Thus, the library of candidate modulators used may include only one type of agent (i.e. peptides), or multiple types (peptides and organic agents). The assay of several candidates at one time is further discussed below.

The present invention provides methods and compositions comprising combining several components. In a preferred embodiment, a preferred combination is tag-ubiquitin, E1, E2, and E3. Preferably the tag is a label, a partner of a binding pair, or a substrate binding molecule. More preferably, the tag is a fluorescent label or a binding pair partner. In a preferred embodiment, the tag is a binding pair partner and the ubiquitin is labeled by indirect labeling. In the indirect labeling embodiment, preferably the label is a fluorescent label or a label enzyme. In an embodiment comprising a label enzyme, preferably the substrate for that enzyme produces a fluorescent product. In a preferred embodiment, the label enzyme substrate is luminol.

In a preferred embodiment, a preferred combination is tag1-ubiquitin, E1, E2 and tag2-E3. Preferably, tag1 is a label, a partner of a binding pair, or a substrate binding molecule and tag2 is a different label, partner of a binding pair, or substrate binding molecule. More preferably, tag1 is a fluorescent label or a member of a binding pair. When tag1 is a member of a binding pair, preferably tag1 is indirectly labeled. Still more preferably, tag-1 is indirectly labeled with a label enzyme. Preferably the label enzyme substrate used to reveal the presence of the enzyme produces a fluorescent product, and more preferably is luminol. In the presently described combination, preferably tag2 is a surface substrate binding element, more preferably a His-tag.

In a preferred embodiment, a preferred combination is tag1-ubiquitin, E1 and tag2-E2. In this embodiment, preferably; tag1 is a label, a partner of a binding pair, or a substrate binding molecule and tag2 is a different label, partner of a binding pair, or substrate binding molecule. More preferably, tag-1 is a label or a member of a binding pair. When tag1 is a member of a binding pair, preferably tag1 is indirectly labeled. In a preferred embodiment, the tag1 label (direct or indirect) is a fluorescent label or a label enzyme. When the tag1 label (direct or indirect) is a label enzyme, preferably the reaction substrate used to reveal the presence of the enzyme produces a fluorescent product, and more preferably is luminol. In the presently described combination, preferably tag2 is a substrate binding element, more preferably a His-tag.

In a preferred embodiment, the compositions of the invention do not comprise a target protein. In this embodiment, ubiquitin is the sole ubiquitination substrate, as discussed above. This differentiates the present assays from all previous ubiquitination enzyme assays, which required addition of a target protein as part of the composition. Because the different combinations of E3 and E2 and combinations of E3 subunits are specific to particular target proteins, the present assays are much more versatile, allowing any variation of such combinations without first identifying the specific target protein to which the combination is directed.

The components of the present compositions may be combined in varying amounts. In a preferred embodiment, ubiquitin is combined at a final concentration of from 20 to 200 ng per 100 $\mu$l reaction solution, most preferable at about 100 ng per 100 $\mu$l reaction solution.

In a preferred embodiment, E1 is combined at a final concentration of from 1 to 50 ng per 100 $\mu$l reaction solution, more preferably from 1 ng to 20 ng per 100 $\mu$l reaction solution, most preferably from 5 ng to 10 ng per 100 $\mu$l reaction solution.

In a preferred embodiment, E2 is combined at a final concentration of 10 to 100 ng per 100 $\mu$l reaction solution, more preferably 10–50 ng per 100 $\mu$l reaction solution.

In a preferred embodiment, E3 is combined at a final concentration of from 1 ng to 500 ng per 100 $\mu$l reaction solution, more preferably from 50 to 400 ng per 100 $\mu$l reaction solution, still more preferably from 100 to 300 ng per 100 $\mu$l reaction solution, most preferably about 100 ng per 100 $\mu$l reaction solution.

The components of the invention are combined under reaction conditions that favor ubiquitin ligase activity. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.5 and 1.5 hours will be sufficient.

A variety of other reagents may be included in the compositions. These include reagents like salts, solvents, buffers, neutral proteins, e.g. albumin, detergents, etc. which may be used to facilitate optimal ubiquitination enzyme activity and/or reduce non-specific or background interactions. Also reagents that otherwise improve the efficiency of the assay, such as protease inhibitors, nuclease inhibitors, anti-microbial agents, etc., may be used. The compositions will also preferably include adenosine tri-phosphate (ATP).

The mixture of components may be added in any order that promotes ubiquitin ligase activity or optimizes identification of candidate modulator effects. In a preferred embodiment, ubiquitin is provided in a reaction buffer solution, followed by addition of the ubiquitination enzymes. In an alternate preferred embodiment, ubiquitin is provided in a reaction buffer solution, a candidate modulator is then added, followed by addition of the ubiquitination enzymes.

Once combined, preferred methods of the invention comprise measuring the amount of ubiquitin bound to E3. In an alternate preferred embodiment in which the combination lacks E3, preferred methods of the invention comprise measuring the amount of ubiquitin bound to E2. As will be understood by one of ordinary skill in the art, the mode of measuring will depend on the specific tag attached to the ubiquitin. As will also be apparent to the skilled artisan, the amount of ubiquitin bound will encompass not only the particular ubiquitin protein bound directly to the ubiquitination enzyme, but also the ubiquitin proteins bound to the former in a polyubiquitin chain.

In a preferred embodiment, the tag attached to the ubiquitin is a fluorescent label. In a preferred embodiment, the tag attached to ubiquitin is an enzyme label or a binding pair member which is indirectly labeled with an enzyme label. In this latter preferred embodiment, the enzyme label substrate produces a fluorescent reaction product. In these preferred embodiments, the amount of ubiquitin bound is measured by luminescence. Equipment for such measurement is commercially available and easily used by one of ordinary skill in the art to make such a measurement.

Other modes of measuring bound ubiquitin are well known in the art and easily identified by the skilled artisan for each of the labels described herein. For instance, radio-isotope labeling may be measured by scintillation counting, or by densitometry after exposure to a photographic emulsion, or by using a device such as a PhosphorImager. Likewise, densitometry may be used to measure bound ubiquitin following a reaction with an enzyme label substrate that produces an opaque product when an enzyme label is used.

In preferred methods of the present invention, E3 is bound to a surface substrate. This may be done directly , as described above for the binding of a label to ubiquitin. This may also be accomplished using tag-E3, wherein the tag is a surface substrate binding molecule.

In another preferred embodiment of the invention, E2 is bound to a surface substrate in the absence of E3. This may be done directly, as described above for the binding of a label to ubiquitin. This may also be accomplished using tag-E2, wherein the tag is a surface substrate binding molecule.

In the two preferred embodiments described immediately above, E3 and E2 are in the form of tag-E3 and tag-E2, respectively, and are bound to a surface substrate via a surface substrate binding molecule tag. In general, any substrate binding molecule can be used. In a preferred embodiment, the tag is a His-tag and the surface substrate is nickel. In a preferred embodiment, the nickel surface substrate is present on the surface of the wells of a multi-well plate, such as a 96 well plate. Such multi-well plates are commercially available. The binding of the enzyme to a surface substrate facilitates the separation of bound ubiquitin from unbound ubiquitin. In the present embodiment, the unbound ubiquitin is easily washed from the receptacle following the ligation reaction. As will be appreciated by those of skill in the art, the use of any surface substrate binding element and receptacle having the surface substrate to which it binds will be effective for facilitating the separation of bound and unbound ubiquitin.

In an alternative embodiment, E3 or E2 is bound, directly or via a substrate binding element, to a bead. Following ligation, the beads may be separated from the unbound ubiquitin and the bound ubiquitin measured. In a preferred embodiment, E3 or E2 is bound to beads and the composition used includes tag-ubiquitin wherein tag is a fluorescent label. In this embodiment, the beads with bound ubiquitin may be separated using a fluorescence-activated cell sorting (FACS) machine. Methods for such use are described in U.S. patent application Ser. No. 09/047,119, which is hereby incorporated in its entirety. The amount of bound ubiquitin can then be measured.

In a preferred embodiment, the compositions of the invention are used to identify ubiquitin ligase activity modulators. In this embodiment, the composition includes a candidate modulator. In a preferred embodiment, the measured amount of tag-ubiquitin bound to E3 is compared with the amount bound when the candidate modulator is absent from the composition, whereby the presence or absence of the modulators effect on ubiquitin ligase activity is determined. In this embodiment, whether the modulator enhances or inhibits ubiquitin ligase activity is also determined.

In a preferred embodiment, the composition of the invention containing a candidate modulator lacks E3 and the amount of ubiquitin bound to E2 is measured. This embodiment may also comprise the step of comparing the amount of ubiquitin bound to E2 in a composition lacking both E3 and the candidate modulator, whereby the modulatory activity of the candidate on ubiquitination enzymes other than E3 is determined. In a preferred embodiment, the percentage difference in the amount of ubiquitin bound to E2 in the presence and absence of the candidate modulator is compared with the percentage difference in the amount bound to E3 in the presence and absence of candidate modulator, whereby the point of effect of the candidate modulator in the enzyme cascade is determined. That is, it is determined whether the candidate modulator affects E3 ubiquitin ligase activity or it affects E1 ubiquitin activating activity and/or E2 ubiquitin conjugating activity.

In a preferred embodiment, multiple assays are performed simultaneously in a high throughput screening system. In this embodiment, multiple assays may be performed in multiple receptacles, such as the wells of a 96 well plate or other multi-well plate. As will be appreciated by one of skill in the art, such a system may be applied to the assay of multiple candidate modulators and/or multiple combination of E3 components and/or E2–E3 pairings. In a preferred embodiment, the present invention is used in a high-throughput screening system for determining the ubiquitin ligase activity of different E2-E3 pairings and/or different E3 component combinations. In an alternate preferred embodiment, the present invention is used in a high throughput screening system for simultaneously testing the effect of individual candidate modulators.

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, blocking steps, etc.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Production of E2, E3 and Ubiquitin

E2 Production

The open reading frame of E2 (Ubc5C) was amplified by PCR and cloned into the pGex-6p-1 *E.Coli.* expression vector (Amersham Pharmacia) as BglII-EcoRI fragments, with N-termninus in frame fused to the GST-tag.

Materials and Methods

Plasmid is transformed in BL21 DE3 competent E.coli (Stratagene, cat# 230132). Cells are grown at 37° C. in TB+100 ug/ml ampicillin and 0.4% glucose to an OD600 of about 0.6, induced with addition of 320 uM IPTG and allowed to grow for another 3 h before harvest. The pellets are washed once with cold PBS, then resuspended in about 6 volumes of lysis buffer (20 mM Tris, 10% glycerol, 0.5 M Nacl, 2.5 mM EDTA, 1 mM TCEP plus Complete—EDTA Free Protease inhibitor tablets, 1 tablet/25 ml of resuspended cells, pH 8.0). The suspension is homogenized and sonicated 3×30 sec. NP40, then added to a final concentration of 0.5 % and the tubes are rocked for 30 min at 4° C. Following centrifugation at 11000 rpm for 25 to 30 min, the supernatant is incubated with Glutathione Sepharose 4B (Amersham, cat# 17–0756–01) at a ratio of 1 ml of beads per 100 ml of original culture volume for 1 to 2 hours at 4° C. with gentle rocking. The beads are pelleted and washed once with 10 bed volumes of the lysis buffer, then twice with 10 bed volumes of Prescission Protease buffer (50 mM Tris-HCL, 50 mM NaCl, 1 mM EDTA, 1 mM DTT, 0.1% NP-40, pH 7.0.). Prescission Protease (Amersham, product# 27–0843) is added at a ratio of 80 ul (160 Units) per ml of GST resin, and allowed to incubate for 4 h at 4° C. The supernatant containing the cleaved E2 protein is collected, and the resin is washed twice with one bed volume of Prescission buffer. All three fractions are analyzed by SDS-PAGE and pooled when appropriate.

Ubiquitin Production

Ubiquitin was cloned into the pFLAG (DYKDDDDK; SEQ ID NO:13)-Mac Expression Vector (Sigma) as a HindIII-EcoRI fragment by PCR. This results in expression of amino-terminal FLAG (DYKDDDDK; SEQ ID NO:13) fusion ubiquitin in *E.Coli.*

Materials and Methods

The induction of protein expression and cell lysis is similar to the above GST-E2 preparation, except that the supernatant is loaded over a FLAG (DYKDDDDK; SEQ ID NO:13)-affinity resin (VVR, cat# IB 13020) at a ratio of 15 ml of beads per 1 L of original culture. The resin is then washed with 10 bed volumes of lysis buffer. The protein is eluted from the column with: 100 mM Acetic acid, 10% glycerol, 200 mM NaCl, 2.5 mM EDTA, 0.1% NP-40, pH 3.5. The elutions are collected as 1 bed volume fractions into tubes that contain $^1/_{10}{}^{th}$ volume of 2 M Tris, 80 mM B-ME, pH 9.0 to neutralize the pH. The elution fractions are analyzed by SDS-PAGE and the appropriate fractions are pooled and dialyzed against 400 volumes of 20 mM Tris, 10% glycerol, 200 mM NaCl, 2.5 mMEDTA, pH 8.0.

Production of E3

Coding sequences for E3 complex were also amplified by PCR and baculoviruses were generated using the Bac-to-Bac system (GibcoBRL). E3 contains two subunits, which are expressed by co-infection of the two baculovirus in the same Hi-5 insect cells. One of the subunit is His-tagged, with the other associating subunit untagged. The detail procedure was done following the Bac to Bac Baculovirus Expression system by GibcoBRL. For example, ROC1 was cloned into the pFastBacHtb vector with a N-terminal His6-tag, while CUL1 was insert into the pFastBac1 vector without any fusing tag. After transposition and Bacmid DNA transfection into SF-9 cells, Baculoviruses were harvested, amplified, and used to co-infect Hi-5 cells for protein expression.

Materials and Methods

Cells are harvested, washed once with cold PBS, and resuspended in about 6 volumes of lysis buffer (20 mM Tris, 20% glycerol, 0.5 M Nacl, 15 mM imidazole, 1 MM TCEP plus Complete—EDTA Free Protease inhibitor tablets, I tablet/25ml of resuspended cells, pH 8.0. ). The suspension is then sonicated 3×30 sec, followed by addition of NP40 to a final concentration of 0.5 % and incubation for 30 min at 4° C. The lysate is then centrifuged and the supernatant is incubated with pre-equilibrated (lysis buffer+NP40) Ni-NTA Agarose beads (Qiagen, cat# 1000632) for 1 to 2 hrs. The pelleted beads are washed 2 times with lysis buffer, resuspended in 1 to 2 volumes of lysis buffer and transferred to a disposable column for elution. Elution is accomplished using 5×1-bed volume aliquots of Lysis buffer+250 mM imidazole. Elution fractions are analyzed by SDS-PAGE and appropriate fractions are pooled. The elution pool is then desalted using either a desalting column or a centrifugal concentration device (more often used for large volumes.) When using centrifugal devices, the eluted pool is diluted 1:1 with lysis buffer that has no imidazole and spun at the appropriate speed until the volume is reduced by half. At this point an equal volume of fresh buffer is added and the device is respun. This is done a total of four times resulting in a 32 fold exchange.

Example 2

Ubiquitin Conjugation Assay

Ubiquitin conjugating activity of E1+E2 was measured using the following protocol with FLAG (DYKDDDDK; SEQ ID NO:13)-ubiquin, purified from *E. coli*, and the E2 Ubch5c, purified as His-Ubch5c from *E. coli.*

Materials and Methods

The following procedures were used for assays measuring ubiquitin conjugation. The wells of Nickel-substrate 96-well plates (Pierce Chemical) are blocked with 100 µl of 1% casein/phosphate buffered saline (PBS) for 1 hour at room temperature, then washed with 200 µl of PBST (0.1% Tween-20 in PBS) 3 times. To each well is added the following FLAG (DYKDDDDK; SEQ ID NO:13)-ubiquitin (see above) reaction solution:
Final Concentration
62.5 mM Tris pH 7.5
6.25 mM MgCl$_2$
0.75 mM DTT
2.5 mM ATP
2.5 mM NaF
12.5 nM Okadaic acid
100 ng FLAG (DYKDDDDK; SEQ ID NO:13)-ubiquitin (made as described above).

To the above solution is then added 10 µl of E1,His-E2 in 20 mM Tris buffer, pH 7.5, and 5% glycerol. His-E2 is made as described above. E1 is obtained commercially (Affiniti Research Products, Exeter, U.K.). The following amounts of each enzyme are used for these assays: 5 ng/well of E1; 25 nl/well E2. The reaction is then allowed to proceed at room temperature for 1 hour.

Following the ubiquitin conjugation reaction, the wells are washed with 200 µl of PBST 3 times. For measurement of the enzyme-bound ubiquitin, 100 µl of Mouse anti-FLAG (DYKDDDDK; SEQ ID NO:13) (1:10,000) and anti-Mouse Ig-HRP (1:15,000) in PBST are added to each well and allowed to incubate at room temperature for 1 hour. The wells are then washed with 200 µl of PBST 3 times, followed by the addition of 100 µl of luminol substrate (1/5 dilution). Luminescence for each well is then measured using a fluorimeter.

Results

Ubiquitin Activating and Conjugating Activity

FIG. 1A shows the luminescence measured for E1 alone and for E1+his-E2, as described above.

Example 3

Ubiquitin Ligase Assay

Ubiquitin ligase activity of E1+E2+E3 was measured using the following protocol with FLAG (DYKDDDDK; SEQ ID NO:13)-ubiquin, purified from *E. coli*, the E2 Ubch5c, purified as GST-Ubch5c from *E. Coli* with the GST tag removed, and the E3 His-ROC/Cul1 complex purified from Hi-5 cells by Baculovirus co-infection. This assay was also used to show the effects of candidate modulators on ubiquitin ligase activity.

Materials and Methods

The wells of Nickel-substrate 96-well plates (Pierce Chemical) are blocked with 100 µl of 1 casein/phosphate buffered saline (PBS) for 1 hour at room temperature, then washed with 200 µl of PBST (0.1% Tween-20 in PBS) 3 times. To each well is added the following FLAG (DYKDDDDK; SEQ ID NO:13)-ubiquitin (see above) reaction solution
Final Concentration
62.5 mM Tris pH 7.5
6.25 mM MgCl$_2$
0.75 mM DYT
2.5 mM ATP
2.5 mM NaF
12.5 nM Okadaic acid
100 ng FLAG (DYKDDDDK; SEQ ID NO:13)-ubiquitin (made as described above).

The buffer solution is brought to a final volume of 80 pl with milipore-filtered water. For assays directed to identifying modulators of ubiquitin ligase activity, 10 µl of a candidate modulator compound in DMSO is then added to the solution. If no candidate modulator is added, 10 µl of DMSO is added to the solution.

To the above solution is then added 10 µl of ubiquitination enzymes in 20 mM Tris buffer, pH 7.5, and 5% glycerol. E2-Ubch5c and E3-HisROC1/Cul1 are made as described above. E1 is obtained commercially (Affiniti Research Products, Exeter, U.K.). The following amounts of each enzyme are used for these assays: 5 ng/well of E1; 25 nl/well E2; and 100 ng/well His-E3. The reaction is then allowed to proceed at room temperature for 1 hour.

Following the ubiquitination reaction, the wells are washed with 200 µl of PBST 3 times. For measurement of the enzyme-bound ubiquitin, 100 µl of Mouse anti-FLAG (DYKDDDDK; SEQ ID NO:13) (1:10,000) and anti-Mouse Ig-HRP (1:15,000) in PBST are added to each well and allowed to incubate at room temperature for 1 hour. The wells are then washed with 200 µl of PBST 3 times, followed by the addition of 100 µl of luminol substrate (1/5 dilution). Luminescence for each well is then measured using a fluorimeter.

Results

Ubiquitin Ligase Activity

FIG. 1 shows the luminescence measured for several different combinations of ubiquitination enzymes. In these experiments, only E3 was in the form His-E3. The luminescence measurements show that the assay specifically measures the activity of the entire ubiquitination enzyme cascade, which requires the presence of all three ubiquitination enzymes in the reaction.

Variations of Composition Components

Figure 2:
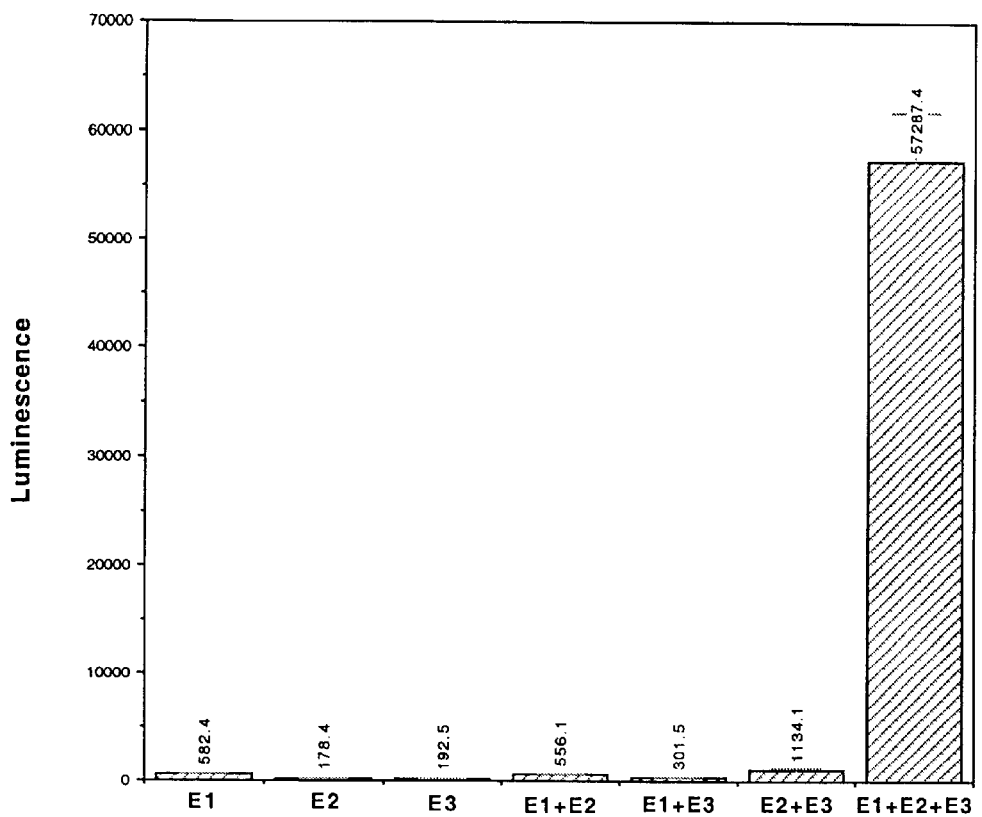
FIG. 2 shows the relative amounts of ubiquitin ligase activity resulting from various combinations of ubiquitination enzymes. In these experiments, E3 comprises the RING finger protein ROC1 and the Cullin Cul1.

FIG. 2A shows the relative effect of varying the amount of E1 on ubiquitin ligase activity in the above procedure, in presence and absence of DMSO. The addition of about 10 ng per 100 µl reaction solution provides maximum ubiquitin ligase activity with the other components of the composition kept as detailed above. The presence of DMSO does not significantly affect the activity of the ubiquitination enzymes.

The relative effect of varying E3 and ubiquitin concentration of the reaction composition is shown in FIG. 2B. Generally speaking, maximum ubiquitin ligase activity was obtained with 200 to 300 ng per 100 µl of E3 at each concentration of ubiquitin, while increasing ubiquitin concentration generally increased ubiquitin ligase activity at each concentration of E3.

Figure 3A:
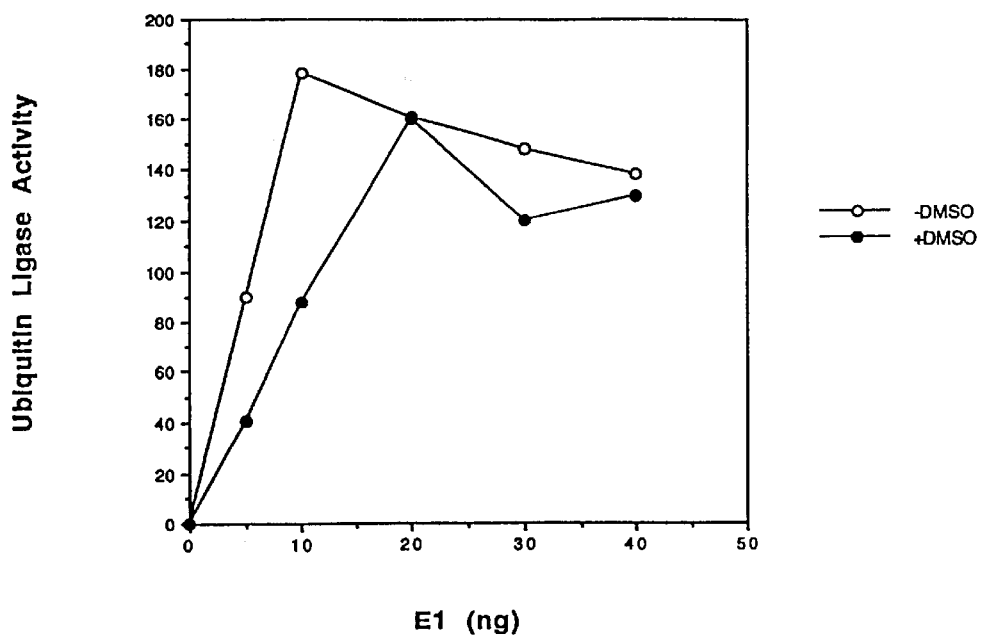
FIG. 3A shows relative ubiquitin ligase activity using varying amounts of E1 in the presence and absence of DMSO.
Figure 3B:
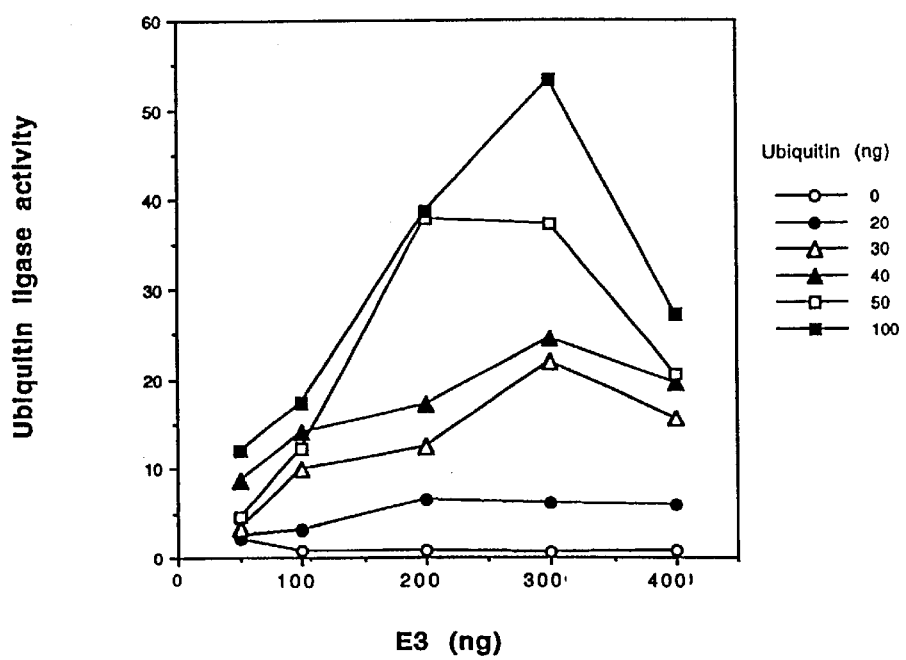
FIG. 3B shows relative ubiquitin ligase activity using varying amounts of ubiquitin and E3.

It was also found that blocking of the wells with 1% casein improved the signal to noise ratio over either no blocking or blocking with 5% bovine serum albumen (BSA). Background was determined after combining all of the components as above except His-E3 and measuring the resulting fluorescence after pre-treating the wells with 5% BSA, 1% casein or nothing. Results are shown in FIG. 3.

Identification of modulators of Ubiquitin Ligase Activity

Figure 4:
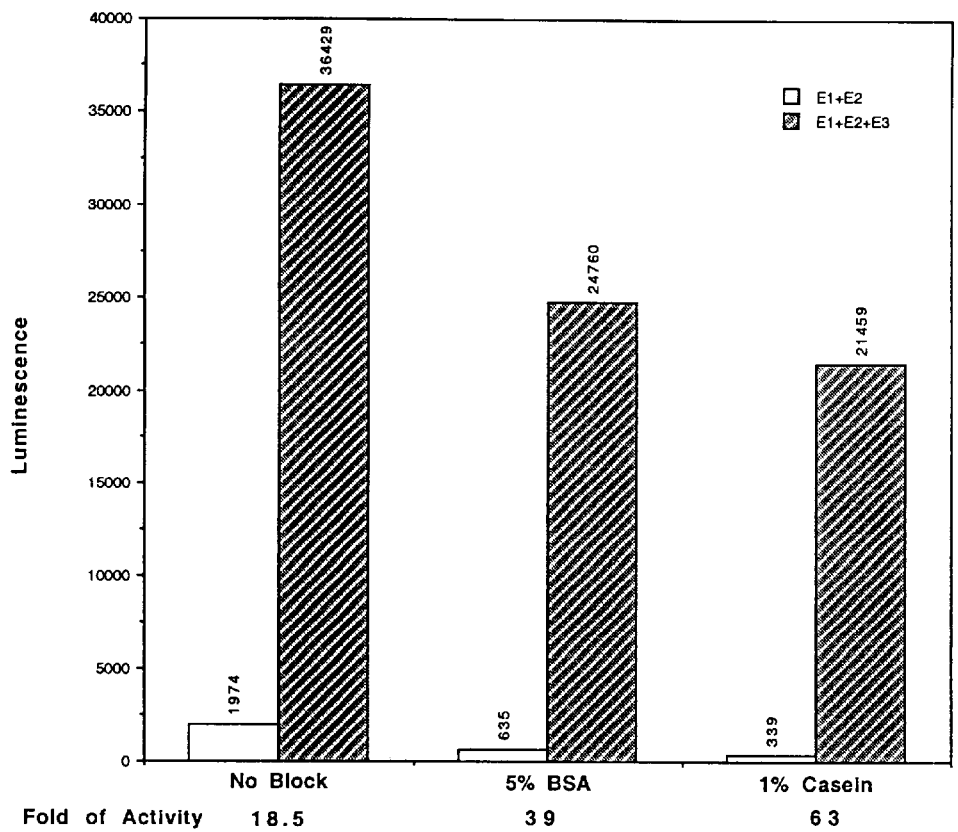
FIG. 4 shows the signal to noise ratio of fluorescent label in a ubiquitin ligase activity assay utilizing FLAG (DYKDDDDK; SEQ ID NO:13)-ubiquitin and an anti-FLAG (DYKDDDDK; SEQ ID NO:13)/anti-mouse antibody conjugated to HRP and Luminol fluorescent HRP substrate. The signal was measured from a reaction composition comprising E1, E2 and E3, which E3 specifically bound the reaction receptacle surface substrate. The background was measured as the amount of fluorescence present after performing the assay in the absence of E3.

To show that the assay is useful for identifying modulators of ubiquitin ligase activity, several candidate modulators were combined at varying concentrations with the assay components as described above. FIG. 4 shows the results from two identified modulators of ubiquitin ligase activity. The modulators decreased ubiquitin ligase activity in a dose-dependent fashion for ubiquitination enzyme compositions comprising either ROC1/Cul1 or ROC2/Cul5 as the E3 component.

Figure 5A:
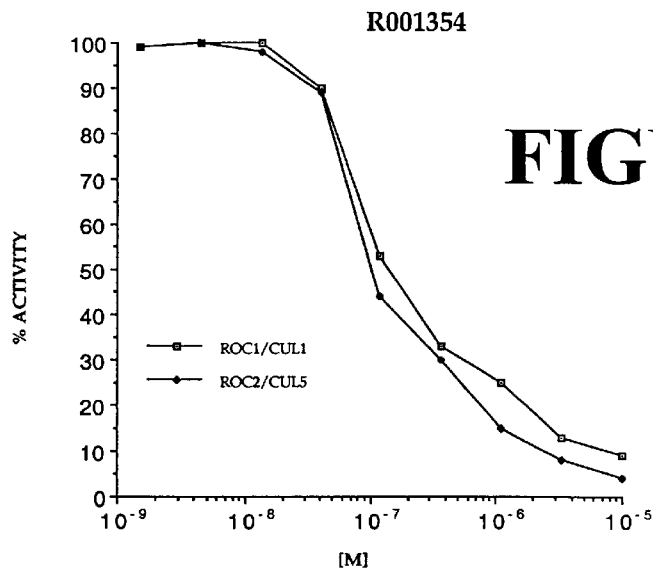
FIG. 5A shows a concentration-dependent reduction in ubiquitin ligase activity in assays comprising either ROC1Cul1 or ROC2/Cul5 as the components of the E3 ubiquitin ligase.
Figure 5B:
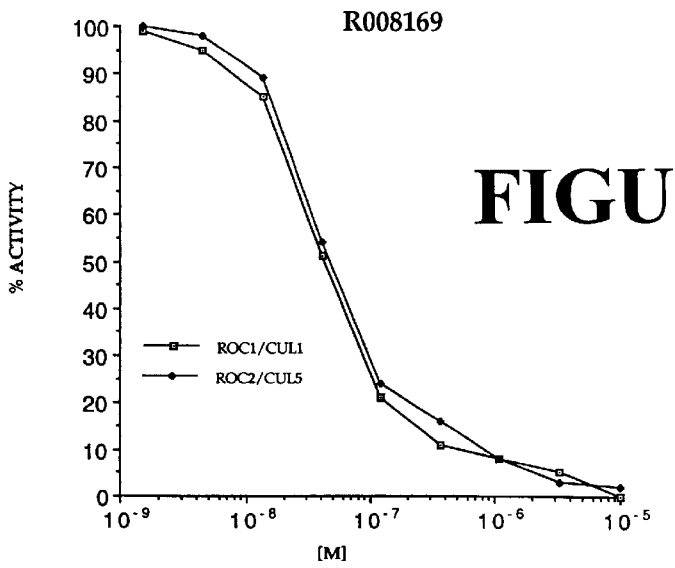
FIG. 5B shows a slightly different pattern of concentration-dependent reduction of ubiquitin ligase activity for another modulator.
Figures 6A, 6B:
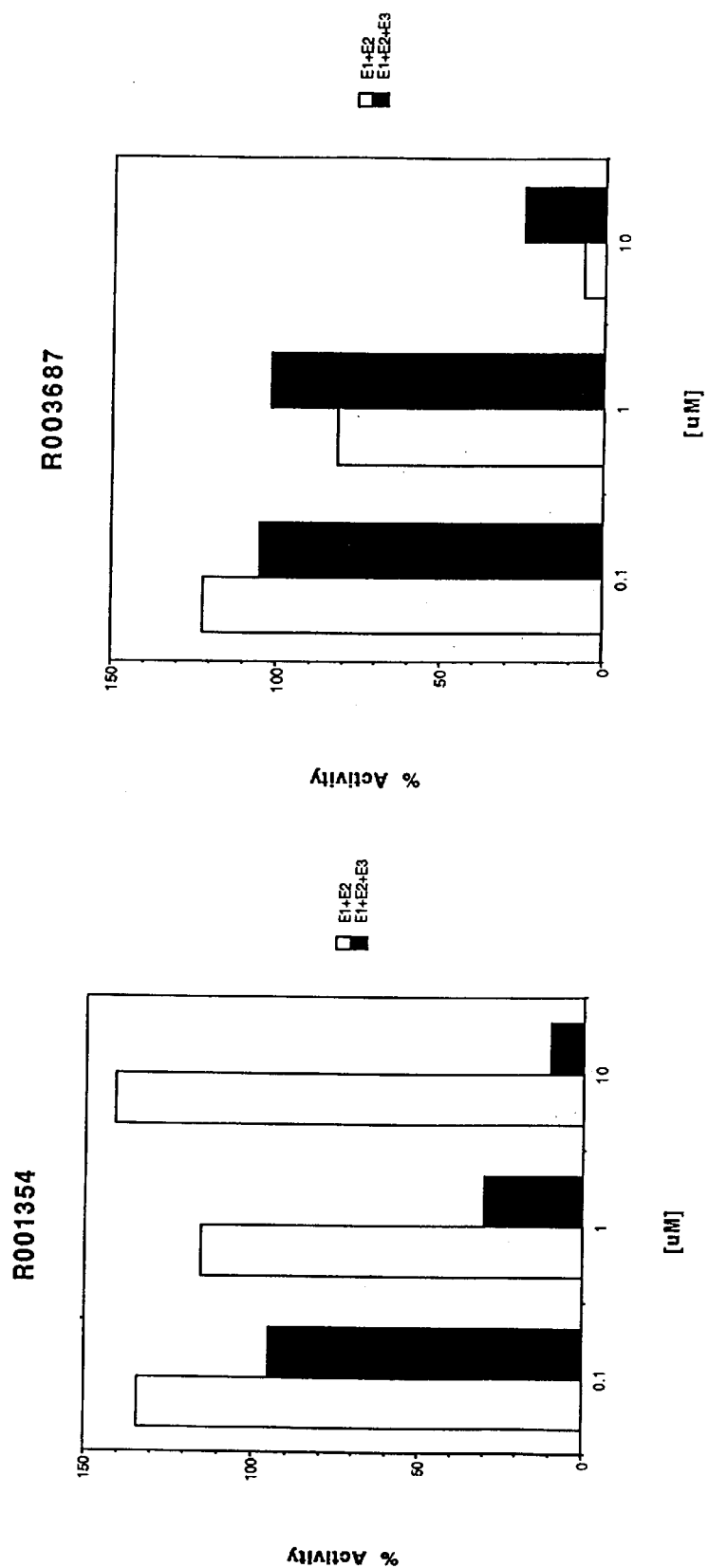
FIG. 6A shows a candidate ubiquitination enzyme modulator that affects only E3.
FIG. 6B shows candidate ubiquitination enzyme modulator that affects enzymes other than E3.
Figure 7A:
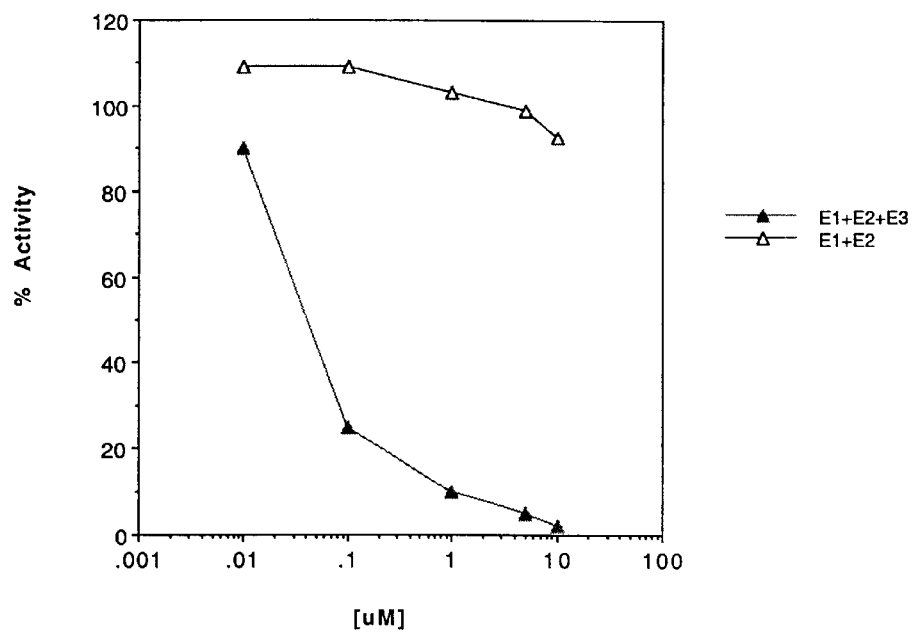
FIG. 7A shows the results for a candidate modulator having a concentration-dependent effect on ubiquitin ligase activity (E1+E2+E3), but not have on ubiquitin conjugating activity (E1+E2), thus affecting only the E3 ligase.
Figure 7B:
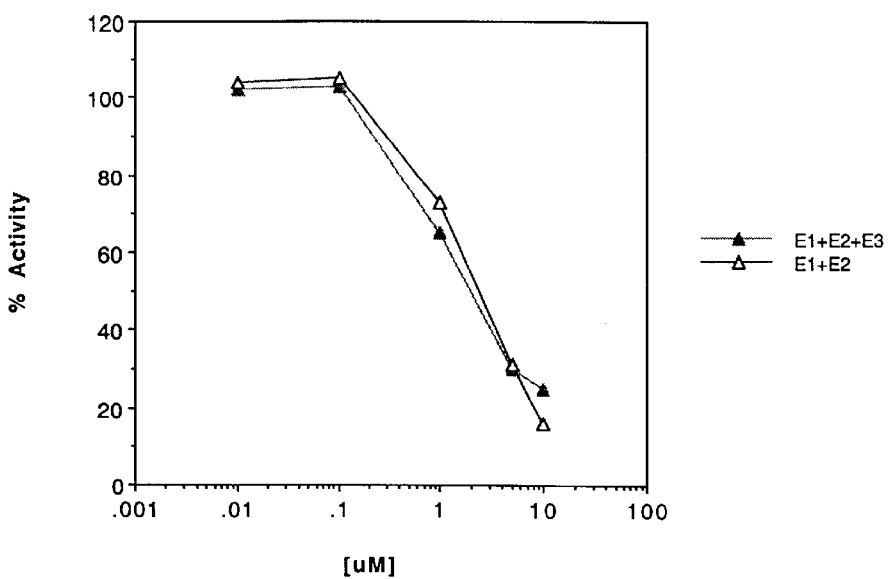
FIG. 7B shows the results for a candidate modulator having a concentration-dependent effect on both ubiquitin conjugating activity and ubiquitin ligase activity, thus affecting a component other than the E3 ligase.

Comparison of the effect of ubiquitin ligase activity modulators on reaction compositions, as described above, either containing E1, E2 and His-E3 or containing E1, His-E2 and lacking E3 shows whether the modulator affects E3 or an enzyme other than E3. In FIG. 5A, the identified modulator decreases ubiquitin ligase activity in the presence of E3, but does not alter activity in the absence of E3, showing that the modulator has a specific effect on E3 ligase activity. In contrast, results shown in FIG. 5B for another modulator reveals that this compound reduces activity whether or not E3 is present, showing that this modulator affects a member of the ubiquitination enzyme cascade other than E3.

We claim:

1. A method of assaying abiquitin ligase activity comprising:
   a) combining:
      i) tag1-ubiquitin;
      ii) ubiquitin activating enzyme (E1);
      iii) ubiquitin conjugating enzyme (E2);
      iv) tag2-ubiquitin ligase (E3);
   b) measuring the amount of said tag1-ubiquitin bound to said ubiquitin ligase (E3), whereby the amount of said tag1-ubiquitin bound to said ubiquitin ligase (E3) indicates said ubiquitin ligase activity.

2. The method of claim 1, further comprising:
   a) combining:
      v) a candidate ubiquitin ligase modulator.

3. The method of claim 1, wherein said tag1 is a label or a partner of a binding pair.

4. The method of claim 3, wherein said label is a fluorescent label.

5. The method of claim 4, wherein said measuring is by measuring luminescence.

6. The method of claim 3, wherein said partner of a binding pair is selected from the group consisting of an antigen, biotin, and calmodalin binding protein (CBP).

7. The method of claim 6, wherein said partner of a binding pair is labeled by indirect labeling.

8. The method of claim 7, wherein said indirect labeling is with a fluorescent label or a label enzyme.

9. The method of claim 8, wherein said measuring is by measuring luminescence.

10. The method of claim 8, wherein said label enzyme is selected from the group consisting of horseradish peroxidase, alkaline phosphatase and glucose oxidase.

11. The method of claim 10, wherein said label enzyme is reacted with a label enzyme substrate which produces a fluorescent product.

12. The method of claim 11, wherein said measuring is by measuring luminescence.

13. The method of claim 12, wherein said tag1 is FALG (DYKDDDDK; SEG ID NO:13).

14. The method of claim 8, wherein said partner of a binding pair is FLAG and said indirect labeling is via anti-FLAG (DYKDDDDK; SEG ID NO:13).

15. The method of claim 7, wherein said partner of a binding pair is FLAG (DYKDDDDK; SEG ID NO:13).

16. The method of claim 6, wherein said antigen is FLAG (DYKDDDDK; SEQ ID NO:13).

17. The method of claim 3, wherein said tag2 is a surface substrate binding molecule.

18. The method of claim 17, wherein said surface substrate binding molecule is a polyhistidine structure (His-tag).

19. The method of claim 18, wherein said assaying is performed in a multi-well plate comprising a surface substrate comprising nickel.

* * * * *

UNITED STATES PATENT AND TRADEMARK OFFICE
CERTIFICATE OF CORRECTION

PATENT NO. : 6,740,495 B1
DATED : May 5, 2004
INVENTOR(S) : Sarkiz D. Issakani et al.

It is certified that error appears in the above-identified patent and that said Letters Patent is hereby corrected as shown below:

Column 59,
Line 35, delete "calmodalin" and substitute therefore -- calmodulin --;

Column 60,
Line 21, delete "FALG" and substitute therefor -- FLAG --;
Lines 25 and 27, delete "SEG" and substitute therefor -- SEQ --;
Line 30, delete "3" and substitute therefor -- 1 --.

Signed and Sealed this

Fifth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,740,495 B1
DATED : May 5, 2004
INVENTOR(S) : Sarkiz D. Issakani et al.

It is certified that error appears in the above-identified patent and that said Letters Patent is hereby corrected as shown below:

<u>Column 60,</u>
Line 30, delete "3" and substitute therefor -- 1 --.

Signed and Sealed this

Thirty-first Day of May, 2005

JON W. DUDAS
*Director of the United States Patent and Trademark Office*

SEQUENCE LISTING

<160> NUMBER OF SEQ ID NOS: 13

<210> SEQ ID NO 1
<211> LENGTH: 3177
<212> TYPE: DNA
<213> ORGANISM: Oryctolagus cuniculus

<400> SEQUENCE: 1

| | | | | | |
|---|---|---|---|---|---|
| atgtccagct | cgccgctgtc | caagaaacgt | cgcgtgtccg | ggcctgatcc | aaagccgggt | 60 |
| tctaactgct | cccctgccca | gtccgtgttg | ccccaagtgc | cctcggcgcc | aaccaacgga | 120 |
| atggcgaaga | acggcagtga | agcagacatc | gatgagggcc | tttactcccg | gcagctgtat | 180 |
| gtgttgggcc | atgaggcgat | gaagcggctc | cagacatcca | gcgttctggt | gtcaggcctg | 240 |
| cggggcctgg | gggtagagat | cgcgaagaac | atcatccttg | gcggggtcaa | ggccgtgacc | 300 |
| ctccatgacc | agggcacggc | ccagtgggct | gacctctcct | cccagttcta | cctgcgagag | 360 |
| gaggacatag | ggaaaaaccg | cgctgaggtg | tcacagcccc | gccttgctga | actcaatagc | 420 |
| tacgtgcctg | tcaccgccta | cactgggccg | ctggttgagg | acttcctcag | tggcttccag | 480 |
| gtggtggtcc | tcactaacag | ccccctggag | gaccagctgc | gcgtgggcga | gttctgtcat | 540 |
| agccgtggca | tcaagctggt | agtggcagac | acgagaggct | tgtttgggca | actcttctgc | 600 |
| gactttggag | aggaaatgat | cctcacagat | tccaacgggg | agcagcccct | cagcaccatg | 660 |
| gtttctatgg | tcaccaagga | caaccctggt | gtggttacct | gcctggatga | ggcccgacat | 720 |
| gggtttgaga | gtggcgattt | tgtttccttc | tccgaagtac | agggcatgac | tgagctcaat | 780 |
| ggaaaccagc | ccatagagat | caaagtcctg | ggtccttaca | cctttagcat | ctgtgacacc | 840 |
| tccaacttct | ccgattacat | ccgtggaggc | attgtcagcc | aggtcaaagt | acctaagaag | 900 |
| ataagcttta | aatccttgtc | agcctcgctg | gcagagcctg | actttgtgat | gacggacttc | 960 |
| gccaagtttt | ctcgccccgc | tcagcttcac | attggcttcc | aggccttgca | caagttctgt | 1020 |
| gcacagcaca | gccggccacc | tagacccagg | aacgaggagg | atgcagcaga | gctggtgacc | 1080 |
| ctagcacgcg | ctgtgaactc | taaagcctcg | tcggcagtgc | agcaagatag | cctggatgag | 1140 |
| gacctcatcc | ggaacctggc | ctttgtggca | gccgggacc | tggcgcccat | caatgccttc | 1200 |
| attgggggcc | tggctgccca | ggaagtcatg | aaggcctgct | ctgggaagtt | tatgcccatc | 1260 |
| atgcagtggc | tgtactttga | tgcccttgag | tgtctcccgg | aggacaaaga | atccctcaca | 1320 |
| gaggacaagt | gcctcccgcg | ccagaaccgt | tatgatgggc | aggtggctgt | gtttggctca | 1380 |
| gacctgcaag | agaagctggg | caggcagaag | tacttcctgg | tgggtgcagg | ggctattggc | 1440 |
| tgtgagctgc | tcaagaactt | tgccatgatt | gggctgggct | gtggtgagaa | cggagaaata | 1500 |
| attgtcacag | acatggacac | cattgagaaa | tctaatctga | accgacagtt | tctattccgg | 1560 |
| ccctgggatg | tcacgaagtt | aaaatctgac | acagctgctg | cagctgtgca | ccagatgaat | 1620 |

-continued

```
ccacatatcc gggtgacaag ccaccagaac cgtgtgggtc ctgacactga acgtatctac   1680
gacgacgatt tcttccaaac tctggatggc gtggccaacg ccttagacaa cgtggatgcc   1740
cgcatgtaca tggaccgccg ctgcgtgtac taccggaagc cgctgctcga atcaggcacc   1800
ctgggcacca agggcaacgt ccaggtggtg atccccttcc tgacagagtc ctacagctcc   1860
agccaagacc cacctgagaa gtccatcccc atctgtaccc tgaagaactt ccccaacgcc   1920
atcgaacaca ctcttcagtg ggctcgggat gaatttgaag gcctcttcaa gcagccagcg   1980
gaaaatgtca accagtacct cacagaccct aagtttgtgg agcggacatt gcggctggcg   2040
ggtacccagc cactggaggt gctggaggct gtgcagcgca gcctggtgct gcagctaccg   2100
cagagctggg cagactgtgt gacctgggcc tgccaccact ggcacaccca gtattctaac   2160
aatatccggc agctgttgca aacttccct cccgaccagc tcacaagctc gggagctccc   2220
ttctggtctg ggcccaaacg ttgtcctcac ccactcacct ttgatgttag caaccctctg   2280
catctggact atgtgatggc tgctgccaac ctgtttgccc agacctacgg gctggcaggc   2340
tctcaggacc gagctgctgt ggccacactc ctgcagtctg tacaggtccc cgagtttacc   2400
cccaagtctg gcgtcaaaat ccacgtttct gaccaggagc tgcagagcgc caatgcttct   2460
gttgacgaca gccgtttaga ggagctcaag gctacgctgc ctagcccga caagctccct   2520 ggattcaaga tgtaccccat tgactttgag aaggatgatg atagtaactt tcacatggac   2580
ttcattgtgg ccgcatccaa cctccgggcc gaaaactatg acattccccc tgcagaccgg   2640
cacaagagca agctgattgc aggaagatc atcccagcca ttgccacgac cacagcagct   2700
gtcgttggcc ttgtgtgtct ggagctgtac aaggtagtgc agggacaccg acacctcgac   2760
tcctacaaga atggtttcct caacctggcc ctgccgtttt tcggtttctc tgaacctctg   2820
gctgcaccac gtcaccagta ctataaccaa gagtggacat tgtgggatcg ctttgaggtt   2880
cagggactgc agcccaacgg tgaggagatg accctcaaac aattcctcga ctactttaag   2940
acagagcaca aattggagat taccatgctg tcccagggtg tgtccatgct ctattccttc   3000
tttatgccag ctgcgaagct caaggaacgg ttggaccagc cgatgacaga gattgtaagc   3060
cgtgtgtcga agcgaaagct gggccgccac gtgcgggcgc tggtgcttga gctgtgctgc   3120
aacgacgaga gcggcgagga cgtcgaagtc ccctacgtcc gatataccat ccgttaa     3177
```

<210> SEQ ID NO 2
<211> LENGTH: 1059
<212> TYPE: PRT
<213> ORGANISM: Oryctolagus cuniculus

<400> SEQUENCE: 2

```
Met Ser Ser Ser Pro Leu Ser Lys Lys Arg Arg Val Ser Gly Pro Asp
 1               5                  10                  15

Pro Lys Pro Gly Ser Asn Cys Ser Pro Ala Gln Ser Val Leu Pro Gln
            20                  25                  30

Val Pro Ser Ala Pro Thr Asn Gly Met Ala Lys Asn Gly Ser Glu Ala
        35                  40                  45

Asp Ile Asp Glu Gly Leu Tyr Ser Arg Gln Leu Tyr Val Leu Gly His
    50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
```

```
                    100                 105                 110
Ser Ser Gln Phe Tyr Leu Arg Glu Glu Asp Ile Gly Lys Asn Arg Ala
        115                 120                 125
Glu Val Ser Gln Pro Arg Leu Ala Glu Leu Asn Ser Tyr Val Pro Val
130                 135                 140
Thr Ala Tyr Thr Gly Pro Leu Val Glu Asp Phe Leu Ser Gly Phe Gln
145                 150                 155                 160
Val Val Val Leu Thr Asn Ser Pro Leu Glu Asp Gln Leu Arg Val Gly
                165                 170                 175
Glu Phe Cys His Ser Arg Gly Ile Lys Leu Val Val Ala Asp Thr Arg
            180                 185                 190
Gly Leu Phe Gly Gln Leu Phe Cys Asp Phe Gly Glu Glu Met Ile Leu
        195                 200                 205
Thr Asp Ser Asn Gly Glu Gln Pro Leu Ser Thr Met Val Ser Met Val
    210                 215                 220
Thr Lys Asp Asn Pro Gly Val Val Thr Cys Leu Asp Glu Ala Arg His
225                 230                 235                 240
Gly Phe Glu Ser Gly Asp Phe Val Ser Phe Ser Glu Val Gln Gly Met
                245                 250                 255
Thr Glu Leu Asn Gly Asn Gln Pro Ile Glu Ile Lys Val Leu Gly Pro
            260                 265                 270
Tyr Thr Phe Ser Ile Cys Asp Thr Ser Asn Phe Ser Asp Tyr Ile Arg
        275                 280                 285
Gly Gly Ile Val Ser Gln Val Lys Val Pro Lys Lys Ile Ser Phe Lys
    290                 295                 300
Ser Leu Ser Ala Ser Leu Ala Glu Pro Asp Phe Val Met Thr Asp Phe
305                 310                 315                 320
Ala Lys Phe Ser Arg Pro Ala Gln Leu His Ile Gly Phe Gln Ala Leu
                325                 330                 335
His Lys Phe Cys Ala Gln His Ser Arg Pro Pro Arg Pro Arg Asn Glu
            340                 345                 350
Glu Asp Ala Ala Glu Leu Val Thr Leu Ala Arg Ala Val Asn Ser Lys
        355                 360                 365
Ala Ser Ser Ala Val Gln Gln Asp Ser Leu Asp Glu Asp Leu Ile Arg
    370                 375                 380
Asn Leu Ala Phe Val Ala Ala Gly Asp Leu Ala Pro Ile Asn Ala Phe
385                 390                 395                 400
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
            420                 425                 430
Pro Glu Asp Lys Glu Ser Leu Thr Glu Asp Lys Cys Leu Pro Arg Gln
        435                 440                 445
Asn Arg Tyr Asp Gly Gln Val Ala Val Phe Gly Ser Asp Leu Gln Glu
    450                 455                 460
Lys Leu Gly Arg Gln Lys Tyr Phe Leu Val Gly Ala Gly Ala Ile Gly
465                 470                 475                 480
Cys Glu Leu Leu Lys Asn Phe Ala Met Ile Gly Leu Gly Cys Gly Glu
                485                 490                 495
Asn Gly Glu Ile Ile Val Thr Asp Met Asp Thr Ile Glu Lys Ser Asn
            500                 505                 510
Leu Asn Arg Gln Phe Leu Phe Arg Pro Trp Asp Val Thr Lys Leu Lys
        515                 520                 525
```

-continued

```
Ser Asp Thr Ala Ala Ala Val His Gln Met Asn Pro His Ile Arg
    530                 535                 540
Val Thr Ser His Gln Asn Arg Val Gly Pro Asp Thr Glu Arg Ile Tyr
545                 550                 555                 560
Asp Asp Asp Phe Phe Gln Thr Leu Asp Gly Val Ala Asn Ala Leu Asp
                565                 570                 575
Asn Val Asp Ala Arg Met Tyr Met Asp Arg Arg Cys Val Tyr Tyr Arg
            580                 585                 590
Lys Pro Leu Leu Glu Ser Gly Thr Leu Gly Thr Lys Gly Asn Val Gln
        595                 600                 605
Val Val Ile Pro Phe Leu Thr Glu Ser Tyr Ser Ser Ser Gln Asp Pro
    610                 615                 620
Pro Glu Lys Ser Ile Pro Ile Cys Thr Leu Lys Asn Phe Pro Asn Ala
625                 630                 635                 640
Ile Glu His Thr Leu Gln Trp Ala Arg Asp Glu Phe Glu Gly Leu Phe
                645                 650                 655
Lys Gln Pro Ala Glu Asn Val Asn Gln Tyr Leu Thr Asp Pro Lys Phe
            660                 665                 670
Val Glu Arg Thr Leu Arg Leu Ala Gly Thr Gln Pro Leu Glu Val Leu
        675                 680                 685
Glu Ala Val Gln Arg Ser Leu Val Leu Gln Leu Pro Gln Ser Trp Ala
    690                 695                 700
Asp Cys Val Thr Trp Ala Cys His His Trp His Thr Gln Tyr Ser Asn
705                 710                 715                 720
Asn Ile Arg Gln Leu Leu His Asn Phe Pro Pro Asp Gln Leu Thr Ser
                725                 730                 735
Ser Gly Ala Pro Phe Trp Ser Gly Pro Lys Arg Cys Pro His Pro Leu
            740                 745                 750
Thr Phe Asp Val Ser Asn Pro Leu His Leu Asp Tyr Val Met Ala Ala
        755                 760                 765
Ala Asn Leu Phe Ala Gln Thr Tyr Gly Leu Ala Gly Ser Gln Asp Arg
    770                 775                 780
Ala Ala Val Ala Thr Leu Leu Gln Ser Val Gln Val Pro Glu Phe Thr
785                 790                 795                 800
Pro Lys Ser Gly Val Lys Ile His Val Ser Asp Gln Glu Leu Gln Ser
                805                 810                 815
Ala Asn Ala Ser Val Asp Asp Ser Arg Leu Glu Glu Leu Lys Ala Thr
            820                 825                 830
Leu Pro Ser Pro Asp Lys Leu Pro Gly Phe Lys Met Tyr Pro Ile Asp
        835                 840                 845
Phe Glu Lys Asp Asp Asp Ser Asn Phe His Met Asp Phe Ile Val Ala
    850                 855                 860
Ala Ser Asn Leu Arg Ala Glu Asn Tyr Asp Ile Pro Pro Ala Asp Arg
865                 870                 875                 880
His Lys Ser Lys Leu Ile Ala Gly Lys Ile Ile Pro Ala Ile Ala Thr
                885                 890                 895
Thr Thr Ala Ala Val Val Gly Leu Val Cys Leu Glu Leu Tyr Lys Val
            900                 905                 910
Val Gln Gly His Arg His Leu Asp Ser Tyr Lys Asn Gly Phe Leu Asn
        915                 920                 925
Leu Ala Leu Pro Phe Phe Gly Phe Ser Glu Pro Leu Ala Ala Pro Arg
    930                 935                 940
```

```
His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
                980                 985                 990

Gly Val Ser Met Leu Tyr Ser Phe Phe Met Pro Ala Ala Lys Leu Lys
                995                 1000                1005

Glu Arg Leu Asp Gln Pro Met Thr Glu Ile Val Ser Arg Val Ser
1010                1015                1020

Lys Arg Lys Leu Gly Arg His Val Arg Ala Leu Val Leu Glu Leu
1025                1030                1035

Cys Cys Asn Asp Glu Ser Gly Glu Asp Val Glu Val Pro Tyr Val
1040                1045                1050

Arg Tyr Thr Ile Arg Glx
        1055
```

<210> SEQ ID NO 3
<211> LENGTH: 444
<212> TYPE: DNA
<213> ORGANISM: Homo sapiens

<400> SEQUENCE: 3

```
atggcgctga aacgattaa taaggaactt agtgatttgg cccgtgaccc tccagcacaa      60
tgttctgcag gtccagttgg ggatgatatg tttcattggc aagccacaat tatgggacct     120
aatgacagcc catatcaagg cggtgtattc tttttgacaa ttcatttcc tacagactac     180
cccttcaaac cacctaaggt tgcatttaca acaagaattt atcatccaaa tattaacagt     240
aatggcagca tttgtctcga tattctaaga tcacagtggt cgcctgcttt aacaatttct     300
aaagttcttt tatccatttg ttcactgcta tgtgatccaa acccagatga ccccctagtg     360
ccagagattg cacggatcta taaaacagac agagataagt acaacagaat atctcgggaa     420
tggactcaga gtatgccat gtga                                             444
```

<210> SEQ ID NO 4
<211> LENGTH: 148
<212> TYPE: PRT
<213> ORGANISM: Homo sapiens

<400> SEQUENCE: 4

```
Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
                20                  25                  30

Trp Gln Ala Thr Ile Met Gly Pro Asn Asp Ser Pro Tyr Gln Gly Gly
            35                  40                  45

Val Phe Phe Leu Thr Ile His Phe Pro Thr Asp Tyr Pro Phe Lys Pro
        50                  55                  60

Pro Lys Val Ala Phe Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
                100                 105                 110

Pro Asn Pro Asp Asp Pro Leu Val Pro Glu Ile Ala Arg Ile Tyr Lys
            115                 120                 125
```

Thr Asp Arg Asp Lys Tyr Asn Arg Ile Ser Arg Glu Trp Thr Gln Lys
            130                 135                 140

Tyr Ala Met Glx
145

<210> SEQ ID NO 5
<211> LENGTH: 84
<212> TYPE: PRT
<213> ORGANISM: Homo sapiens

<400> SEQUENCE: 5

Met Lys Val Lys Ile Lys Cys Trp Asn Gly Val Ala Thr Trp Leu Trp
1               5                   10                  15

Val Ala Asn Asp Glu Asn Cys Gly Ile Cys Arg Met Ala Phe Asn Gly
                20                  25                  30

Cys Cys Pro Asp Cys Lys Val Pro Gly Asp Asp Cys Pro Leu Val Trp
            35                  40                  45

Gly Gln Cys Ser His Cys Phe His Met His Cys Ile Leu Lys Trp Leu
        50                  55                  60

His Ala Gln Gln Val Gln Gln His Cys Pro Met Cys Arg Gln Thr Trp
65                  70                  75                  80

Lys Phe Lys Glu

<210> SEQ ID NO 6
<211> LENGTH: 108
<212> TYPE: PRT
<213> ORGANISM: Homo sapiens

<400> SEQUENCE: 6

Met Ala Ala Met Asp Val Asp Thr Pro Ser Gly Thr Asn Ser Gly
1               5                   10                  15

Ala Gly Lys Lys Arg Phe Glu Val Lys Lys Trp Asn Ala Val Ala Leu
                20                  25                  30

Trp Ala Trp Asp Ile Val Val Asp Asn Cys Ala Ile Cys Arg Asn His
            35                  40                  45

Ile Met Asp Leu Cys Ile Glu Cys Gln Ala Asn Gln Ala Ser Ala Thr
        50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Glu Phe Gln Lys Tyr Gly His
            100                 105

<210> SEQ ID NO 7
<211> LENGTH: 342
<212> TYPE: DNA
<213> ORGANISM: Homo sapiens

<400> SEQUENCE: 7
atggccgacg tggaagacgg agaggaaacc tgcgccctgg cctctcactc cgggagctca      60
ggctcaacgt cggaggcga caagatgttc tccctcaaga gtggaaccc ggtggccatg     120 tggagctggg acgtggagtg cgatacgtgc gccatctgca gggtccaggt gatggatgcc     180
tgtcttagat gtcaagctga aaacaaacaa gaggactgtg ttgtggtctg gggagaatgt     240
aatcattcct tccacaactg ctgcatgtcc ctgtgggtga aacagaacaa tcgctgccct     300
ctctgccagc aggactgggt ggtccaaaga atcggcaaat ga                         342

<210> SEQ ID NO 8
<211> LENGTH: 113
<212> TYPE: PRT
<213> ORGANISM: Homo sapiens

<400> SEQUENCE: 8

Met Ala Asp Val Glu Asp Gly Glu Glu Thr Cys Ala Leu Ala Ser His
1               5                   10                  15

Ser Gly Ser Ser Gly Ser Thr Ser Gly Gly Asp Lys Met Phe Ser Leu
            20                  25                  30

Lys Lys Trp Asn Pro Val Ala Met Trp Ser Trp Asp Val Glu Cys Asp
        35                  40                  45

Thr Cys Ala Ile Cys Arg Val Gln Val Met Asp Ala Cys Leu Arg Cys
    50                  55                  60

Gln Ala Glu Asn Lys Gln Glu Asp Cys Val Val Val Trp Gly Glu Cys
65                  70                  75                  80

Asn His Ser Phe His Asn Cys Cys Met Ser Leu Trp Val Lys Gln Asn
                85                  90                  95

Asn Arg Cys Pro Leu Cys Gln Gln Asp Trp Val Val Gln Arg Ile Gly
            100                 105                 110

Lys

<210> SEQ ID NO 9
<211> LENGTH: 2343
<212> TYPE: DNA
<213> ORGANISM: Homo sapiens

<400> SEQUENCE: 9
atggcgacgt ctaatctgtt aaagaataaa ggttctcttc agtttgaaga caaatgggat     60
tttatgcgcc cgattgtttt gaagctttta cgccaggaat ctgttacaaa acagcagtgg    120
tttgatctgt tttcggatgt gcatgcagtc tgtctttggg atgataaagg cccagcaaaa    180
attcatcagg ctttaaaaga agatattctt gagtttatta agcaggcaca ggcacgagta    240
ctgagccatc aagatgatac ggctttgcta aaagcatata ttgttgaatg gcgaaagttc    300
tttacacaat gtgatatttt accaaaacct ttttgtcaac tagagattac tttaatgggt    360
aaacagggca gcaataaaaa atcaaatgtg aagacagta ttgttcgaaa gcttatgctt    420
gatacatgga atgagtcaat cttttcaaac ataaaaaaca gactccaaga tagtgcaatg    480
aagctggtac atgctgagag attgggagaa gcttttgatt ctcagctggt tattggagta    540
agagaatcct atgttaacct tgttctaat cctgaggata aacttcaaat ttatagggac     600
aattttgaga aggcatactt ggattcaaca gagagatttt atagaacaca agcaccctcg    660
tatttacaac caaatggtgt acagaattat atgaaatatg cagatgctaa attaaaagaa    720
gaagaaaaac gagcactacg ttatttagaa acaagacgag aatgtaactc cgttgaagca    780
ctcatggaat gctgtgtaaa tgccctggtg acatcattta aagagactat cttagctgag    840
tgccaaggca tgatcaagag aaatgaaact gaaaaattac atttaatgtt tcattgatg     900 gacaaagttc ctaatggtat agagccaatg ttgaaagact ggaggaaca tatcattagt     960 gctggcctgg cagatatggt agcagctgct gaaactatta ctactgactc tgagaaatac   1020
gttgagcagt tacttacact atttaataga tttagtaaac tcgtcaaaga agcttttcaa   1080
gatgatccac gatttcttac tgcaagagat aaggcgtata aagcagttgt taatgatgct   1140

-continued

```
accatattta aacttgaatt acctttgaag cagaagggg tgggattaaa aactcagcct   1200
gaatcaaaat gccctgagct gcttgccaat tactgtgaca tgttgctaag aaaaacacca   1260
ttaagcaaaa aactaacctc tgaagagatt gaagcaaagc ttaaagaagt gctcttggta   1320
cttaagtatg tacagaacaa agatgttttt atgaggtatc ataaagctca tttgacacga   1380
cgtcttatat tagacatctc tgccgatagt gaaattgaag aaaacatggt agagtggcta   1440
agagaagttg gtatgccagc ggattatgta aacaagcttg ctagaatgtt tcaggacata   1500
aaagtatctg aagatttgaa ccaagctttt aaggaaatgc acaaaaataa taaattggca   1560
ttaccagctg attcagttaa tataaaaatt ctgaatgctg gcgcctggtc aagaagttct   1620
gagaaagtct ttgtctcact tcctactgaa ctggaggact tgataccgga agtagaagaa   1680
ttctacaaaa aaaatcatag tggtagaaaa ttacattggc atcatctcat gtcaaatgga   1740
attataacat ttaagaatga agttggtcaa tatgatttgg aggtaaccac gtttcagctc   1800
gctgtattgt ttgcatggaa ccaaagaccc agagagaaaa tcagctttga aaatcttaag   1860
cttgcaactg aactccctga tgctgaactt aggaggactt tatggtcttt agtagctttc   1920
ccaaaactca aacggcaagt ttttttgtat gaccctcaag tcaactcacc caaagacttt   1980
acagaaggta ccctcttctc agtgaaccag gagttcagtt taataaaaaa tgcaaaggtt   2040
cagaaaaggg gtaaaatcaa cttgattgga cgtttgcagc tcactacaga aaggatgaga   2100
gaagaagaga atgaaggaat agttcaacta cgaatactaa gaacccagga agctatcata   2160
caaataatga aaatgagaaa gaaaattagt aatgctcagc tgcagactga attagtagaa   2220
attttgaaaa acatgttctt gccacaaaag aaaatgataa aagagcaaat agagtggcta   2280
atagagcaca aatacatcag aagagatgaa tctgatatca cactttcat atatatggca   2340 taa                                                                  2343
```

<210> SEQ ID NO 10
<211> LENGTH: 861
<212> TYPE: PRT
<213> ORGANISM: Homo sapiens

<400> SEQUENCE: 10

```
Met Arg Ser Phe Ala Trp Gly Ser Ser Gly Asp His Val Gly Asp Lys
1               5                   10                  15

Ser Glu Glu Ala Pro Gly Ala Trp Asp Glu Val Ser Ala Val Gly Ala
            20                  25                  30

Leu Leu Gln Arg Pro Pro His Pro Gly Ala Gly Pro Thr Gly Pro Gly
        35                  40                  45

Pro Trp Trp Glu Leu Arg Pro Val Lys Ala Trp Pro Gly Arg Glu
    50                  55                  60

Arg His Glu Phe Ser Arg Arg Leu Val Ser Arg Glu Ser Lys Leu Lys
65                  70                  75                  80

Asn Met Ala Thr Ser Asn Leu Leu Lys Asn Lys Gly Ser Leu Gln Phe
                85                  90                  95

Glu Asp Lys Trp Asp Phe Met Arg Pro Ile Val Leu Lys Leu Leu Arg
            100                 105                 110

Gln Glu Ser Val Thr Lys Gln Gln Trp Phe Asp Leu Phe Ser Asp Val
        115                 120                 125

His Ala Val Cys Leu Trp Asp Asp Lys Gly Pro Ala Lys Ile His Gln
    130                 135                 140

Ala Leu Lys Glu Asp Ile Leu Glu Phe Ile Lys Gln Ala Gln Ala Arg
145                 150                 155                 160
```

```
Val Leu Ser His Gln Asp Asp Thr Ala Leu Leu Lys Ala Tyr Ile Val
                165                 170                 175

Glu Trp Arg Lys Phe Phe Thr Gln Cys Asp Ile Leu Pro Lys Pro Phe
            180                 185                 190

Cys Gln Leu Glu Ile Thr Leu Met Gly Lys Gln Gly Ser Asn Lys Lys
        195                 200                 205

Ser Asn Val Glu Asp Ser Ile Val Arg Lys Leu Met Leu Asp Thr Trp
    210                 215                 220

Asn Glu Ser Ile Phe Ser Asn Ile Lys Asn Arg Leu Gln Asp Ser Ala
225                 230                 235                 240

Met Lys Leu Val His Ala Glu Arg Leu Gly Glu Ala Phe Asp Ser Gln
                245                 250                 255

Leu Val Ile Gly Val Arg Glu Ser Tyr Val Asn Leu Cys Ser Asn Pro
                260                 265                 270

Glu Asp Lys Leu Gln Ile Tyr Arg Asp Asn Phe Glu Lys Ala Tyr Leu
                275                 280                 285

Asp Ser Thr Glu Arg Phe Tyr Arg Thr Gln Ala Pro Ser Tyr Leu Gln
            290                 295                 300

Pro Asn Gly Val Gln Asn Tyr Met Lys Tyr Ala Asp Ala Lys Leu Lys
305                 310                 315                 320

Glu Glu Glu Lys Arg Ala Leu Arg Tyr Leu Glu Thr Arg Arg Glu Cys
                325                 330                 335

Asn Ser Val Glu Ala Leu Met Glu Cys Cys Val Asn Ala Leu Val Thr
                340                 345                 350

Ser Phe Lys Glu Thr Ile Leu Ala Glu Cys Gln Gly Met Ile Lys Arg
                355                 360                 365

Asn Glu Thr Glu Lys Leu His Leu Met Phe Ser Leu Met Asp Lys Val
            370                 375                 380

Pro Asn Gly Ile Glu Pro Met Leu Lys Asp Leu Glu Glu His Ile Ile
385                 390                 395                 400

Ser Ala Gly Leu Ala Asp Met Val Ala Ala Glu Thr Ile Thr Thr
                405                 410                 415

Asp Ser Glu Lys Tyr Val Glu Gln Leu Leu Thr Leu Phe Asn Arg Phe
            420                 425                 430

Ser Lys Leu Val Lys Glu Ala Phe Gln Asp Asp Pro Arg Phe Leu Thr
        435                 440                 445

Ala Arg Asp Lys Ala Tyr Lys Ala Val Val Asn Asp Ala Thr Ile Phe
    450                 455                 460

Lys Leu Glu Leu Pro Leu Lys Gln Lys Gly Val Gly Leu Lys Thr Gln
465                 470                 475                 480

Pro Glu Ser Lys Cys Pro Glu Leu Leu Ala Asn Tyr Cys Asp Met Leu
                485                 490                 495

Leu Arg Lys Thr Pro Leu Ser Lys Lys Leu Thr Ser Glu Glu Ile Glu
                500                 505                 510

Ala Lys Leu Lys Glu Val Leu Leu Val Leu Lys Tyr Val Gln Asn Lys
                515                 520                 525

Asp Val Phe Met Arg Tyr His Lys Ala His Leu Thr Arg Arg Leu Ile
            530                 535                 540

Leu Asp Ile Ser Ala Asp Ser Glu Ile Glu Glu Asn Met Val Glu Trp
545                 550                 555                 560

Leu Arg Glu Val Gly Met Pro Ala Asp Tyr Val Asn Lys Leu Ala Arg
                565                 570                 575
```

Met Phe Gln Asp Ile Lys Val Ser Glu Asp Leu Asn Gln Ala Phe Lys
                580                 585                 590

Glu Met His Lys Asn Asn Lys Leu Ala Leu Pro Ala Asp Ser Val Asn
            595                 600                 605

Ile Lys Ile Leu Asn Ala Gly Ala Trp Ser Arg Ser Ser Glu Lys Val
610                 615                 620

Phe Val Ser Leu Pro Thr Glu Leu Glu Asp Leu Ile Pro Glu Val Glu
625                 630                 635                 640

Glu Phe Tyr Lys Lys Asn His Ser Gly Arg Lys Leu His Trp His His
                645                 650                 655

Leu Met Ser Asn Gly Ile Ile Thr Phe Lys Asn Glu Val Gly Gln Tyr
                660                 665                 670

Asp Leu Glu Val Thr Thr Phe Gln Leu Ala Val Leu Phe Ala Trp Asn
            675                 680                 685

Gln Arg Pro Arg Glu Lys Ile Ser Phe Glu Asn Leu Lys Leu Ala Thr
            690                 695                 700

Glu Leu Pro Asp Ala Glu Leu Arg Arg Thr Leu Trp Ser Leu Val Ala
705                 710                 715                 720

Phe Pro Lys Leu Lys Arg Gln Val Phe Leu Tyr Asp Pro Gln Val Asn
                725                 730                 735

Ser Pro Lys Asp Phe Thr Glu Gly Thr Leu Phe Ser Val Asn Gln Glu
            740                 745                 750

Phe Ser Leu Ile Lys Asn Ala Lys Val Gln Lys Arg Gly Lys Ile Asn
            755                 760                 765

Leu Ile Gly Arg Leu Gln Leu Thr Thr Glu Arg Met Arg Glu Glu Glu
770                 775                 780

Asn Glu Gly Ile Val Gln Leu Arg Ile Leu Arg Thr Gln Glu Ala Ile
785                 790                 795                 800

Ile Gln Ile Met Lys Met Arg Lys Lys Ile Ser Asn Ala Gln Leu Gln
                805                 810                 815

Thr Glu Leu Val Glu Ile Leu Lys Asn Met Phe Leu Pro Gln Lys Lys
            820                 825                 830

Met Ile Lys Glu Gln Ile Glu Trp Leu Ile Glu His Lys Tyr Ile Arg
            835                 840                 845

Arg Asp Glu Ser Asp Ile Asn Thr Phe Ile Tyr Met Ala
850                 855                 860

<210> SEQ ID NO 11
<211> LENGTH: 2469
<212> TYPE: DNA
<213> ORGANISM: Homo sapiens

<400> SEQUENCE: 11
atggcggcgg cagttgtggt ggcggagggg gacagcgact cccggcccgg acaggagttg      60
ttagtggcct ggaacaccgt gagcaccggc ctggtgccgc cggctgcgct ggggctggtg     120
tcttcccgga ccagcggtgc agtcccgcca aggaagagg agctccgggc ggcggtggag     180
gttctgaggg gccacgggct acactcggtc ctggaggagt ggttcgtgga ggtgctgcag     240
aacgatctgc aggccaacat ctcccctgag ttctggaatg ccatctccca atgcgagaac     300
tctgcggatg agcccagtg cctttttgcta ctccttgacg cttttggcct gctggagagc     360
cgcctggatc cctacctgcg tagcctagag ctgctggaga atggactcg cctgggcttg     420 ctgatgggca ctggtgctca gggctgcga gaagaagtcc acactatgtt gcgcggagtc     480
ttgttcttta gcaccccag aaccttccaa gagatgatcc agcgtctgta tgggtgcttc     540

```
ttgagagtct atatgcagag taagaggaag ggggaagggg gcacagaccc ggaactggaa    600
ggggagctgg acagccggta tgcccgtcgc cggtactacc ggctcctgca gagcccgctg    660
tgtgcagggt gcagcagtga caagcaacag tgctggtgtc gccaggctct ggagcagttc    720
catcagctca gccaggtctt acacaggctc agtctgctgg agcgggtcag tgccgaggct    780
gtgaccacca ccctgcacca ggtgacccgg agaggatgag gaccgttg ccggggcgag     840 tacgagcgct ccttcctgcg tgagttccac aagtggatcg agcgggtggt cggctggctc    900
ggcaaggtgt cctgcagga cggccccgcc aggcccgcat ctcccgaggc cggcaacacc     960
ctgcgccgct ggcgctgcca cgtgcaaagg ttcttctacc gcatctacgc cagcctgcgc    1020
atcgaggagc tcttcagcat cgtccgagac ttcccagact cccggccagc catcgaggac    1080
ctcaagtact gcctggagag gacggaccag aggcagcagc tgctcgtgtc cctcaaggct    1140
gccctggaga ctcggctcct gcatccaggc gtcaacacgt gtgacatcat caccctctat    1200
atctctgcca tcaaggcgct gcgcgtgctg gacccttcca tggtcatcct ggaggtggcc    1260
tgtgagccta tccgccgcta cctgaggacg cgggaggaca cagtgcggca gattgtggct    1320
gggctgacgg gggactcgga cgggacaggg gacctggctg ttgagctgtc caagaccgac    1380
ccggcgagcc tggagacagg ccaggacagt gaggatgact caggcgagcc agaggactgg    1440
gtcccggacc ctgtggatgc cgatccaggg aagtcgagct ccaagcggcg ttcatcggac    1500
atcatcagcc tgctggtcag catctacggc agcaaggacc tcttcatcaa tgagtaccgc    1560
tcgctgctgg ccgaccgcct gctgcaccag ttcagcttca gccccgagcg ggagatccgc    1620
aacgtggagc tgctgaagct gcgctttggc gaggccccaa tgcacttctg tgaagtcatg    1680
ctgaaggaca tggcggactc ccgccgcatc aatgccaaca tccgggagga ggatgagaag    1740
cggccagcag aggagcagcc accgttcggg gtctacgctg tcatcctgtc cagtgagttc    1800
tggccgccct tcaaggacga gaagctggag gtccccgagg atatcagggc agccctggag    1860
gcttactgca agaagtatga gcagctcaag gccatgcgga ccctcagttg gaagcacacc    1920
ctgggcctgg tgaccatgga cgtggagctg gccgaccgca cgctgtctgt ggcggtcacc    1980
ccagtacagg cggtgatctt gctgtatttt caggaccaag ccagctggac cctggaggaa    2040
ctgagcaagg cggtgaaaat gcccgtggcg ctgctgcggc ggcggatgtc cgtgtggctg    2100
cagcagggtg tgctgcgtga ggagccccc ggcaccttct ctgtcattga ggaggagcgg    2160
cctcaggacc gggacaacat ggtgctcatt gacagtgacg acgagagcga ctccggcatg    2220
gcctcccagg ccgaccagaa ggaggaggag ctgctgctct tctggacgta catccaggcc    2280
atgctgacca acctggagag cctctcactg gatcgtatct acaacatgct ccgcatgttt    2340
gtggtgactg ggcctgcact ggccgagatt gacctgcagg agctgcaggg ctacctgcag    2400
aagaaggtgc gggaccagca gctcgtctac tcggccggcg tctaccgcct gcccaagaac    2460
tgcagctga                                                            2469
```

<210> SEQ ID NO 12
<211> LENGTH: 822
<212> TYPE: PRT
<213> ORGANISM: Homo sapiens

<400> SEQUENCE: 12

Met Ala Ala Ala Val Val Val Ala Glu Gly Asp Ser Asp Ser Arg Pro
1               5                   10                  15

Gly Gln Glu Leu Leu Val Ala Trp Asn Thr Val Ser Thr Gly Leu Val

```
                20                  25                  30
Pro Pro Ala Ala Leu Gly Leu Val Ser Ser Arg Thr Ser Gly Ala Val
         35                  40                  45

Pro Pro Lys Glu Glu Leu Arg Ala Ala Val Glu Val Leu Arg Gly
 50                  55                  60

His Gly Leu His Ser Val Leu Glu Glu Trp Phe Val Glu Val Leu Gln
 65                  70                  75                  80

Asn Asp Leu Gln Ala Asn Ile Ser Pro Glu Phe Trp Asn Ala Ile Ser
                 85                  90                  95

Gln Cys Glu Asn Ser Ala Asp Glu Pro Gln Cys Leu Leu Leu Leu Leu
                100                 105                 110

Asp Ala Phe Gly Leu Leu Glu Ser Arg Leu Asp Pro Tyr Leu Arg Ser
        115                 120                 125

Leu Glu Leu Leu Glu Lys Trp Thr Arg Leu Gly Leu Leu Met Gly Thr
        130                 135                 140

Gly Ala Gln Gly Leu Arg Glu Glu Val His Thr Met Leu Arg Gly Val
145                 150                 155                 160

Leu Phe Phe Ser Thr Pro Arg Thr Phe Gln Glu Met Ile Gln Arg Leu
                165                 170                 175

Tyr Gly Cys Phe Leu Arg Val Tyr Met Gln Ser Lys Arg Lys Gly Glu
                180                 185                 190

Gly Gly Thr Asp Pro Glu Leu Glu Gly Glu Leu Asp Ser Arg Tyr Ala
        195                 200                 205

Arg Arg Arg Tyr Tyr Arg Leu Leu Gln Ser Pro Leu Cys Ala Gly Cys
210                 215                 220

Ser Ser Asp Lys Gln Gln Cys Trp Cys Arg Gln Ala Leu Glu Gln Phe
225                 230                 235                 240

His Gln Leu Ser Gln Val Leu His Arg Leu Ser Leu Leu Glu Arg Val
                245                 250                 255

Ser Ala Glu Ala Val Thr Thr Thr Leu His Gln Val Thr Arg Glu Arg
                260                 265                 270

Met Glu Asp Arg Cys Arg Gly Glu Tyr Glu Arg Ser Phe Leu Arg Glu
        275                 280                 285

Phe His Lys Trp Ile Glu Arg Val Val Gly Trp Leu Gly Lys Val Phe
        290                 295                 300

Leu Gln Asp Gly Pro Ala Arg Pro Ala Ser Pro Glu Ala Gly Asn Thr
305                 310                 315                 320

Leu Arg Arg Trp Arg Cys His Val Gln Arg Phe Phe Tyr Arg Ile Tyr
                325                 330                 335

Ala Ser Leu Arg Ile Glu Glu Leu Phe Ser Ile Val Arg Asp Phe Pro
        340                 345                 350

Asp Ser Arg Pro Ala Ile Glu Asp Leu Lys Tyr Cys Leu Glu Arg Thr
        355                 360                 365

Asp Gln Arg Gln Gln Leu Leu Val Ser Leu Lys Ala Ala Leu Glu Thr
        370                 375                 380

Arg Leu His Pro Gly Val Asn Thr Cys Asp Ile Ile Thr Leu Tyr
385                 390                 395                 400

Ile Ser Ala Ile Lys Ala Leu Arg Val Leu Asp Pro Ser Met Val Ile
                405                 410                 415

Leu Glu Val Ala Cys Glu Pro Ile Arg Arg Tyr Leu Arg Thr Arg Glu
                420                 425                 430

Asp Thr Val Arg Gln Ile Val Ala Gly Leu Thr Gly Asp Ser Asp Gly
        435                 440                 445
```

```
Thr Gly Asp Leu Ala Val Glu Leu Ser Lys Thr Asp Pro Ala Ser Leu
    450                 455                 460

Glu Thr Gly Gln Asp Ser Glu Asp Ser Gly Glu Pro Glu Asp Trp
465                 470                 475                 480

Val Pro Asp Pro Val Asp Ala Asp Pro Gly Lys Ser Ser Lys Arg
                485                 490                 495

Arg Ser Ser Asp Ile Ile Ser Leu Leu Val Ser Ile Tyr Gly Ser Lys
                500                 505                 510

Asp Leu Phe Ile Asn Glu Tyr Arg Ser Leu Leu Ala Asp Arg Leu Leu
        515                 520                 525

His Gln Phe Ser Phe Ser Pro Glu Arg Glu Ile Arg Asn Val Glu Leu
        530                 535                 540

Leu Lys Leu Arg Phe Gly Glu Ala Pro Met His Phe Cys Glu Val Met
545                 550                 555                 560

Leu Lys Asp Met Ala Asp Ser Arg Arg Ile Asn Ala Asn Ile Arg Glu
                565                 570                 575

Glu Asp Glu Lys Arg Pro Ala Glu Glu Gln Pro Pro Phe Gly Val Tyr
                580                 585                 590

Ala Val Ile Leu Ser Ser Glu Phe Trp Pro Pro Phe Lys Asp Glu Lys
        595                 600                 605

Leu Glu Val Pro Glu Asp Ile Arg Ala Ala Leu Glu Ala Tyr Cys Lys
610                 615                 620

Lys Tyr Glu Gln Leu Lys Ala Met Arg Thr Leu Ser Trp Lys His Thr
625                 630                 635                 640

Leu Gly Leu Val Thr Met Asp Val Glu Leu Ala Asp Arg Thr Leu Ser
                645                 650                 655

Val Ala Val Thr Pro Val Gln Ala Val Ile Leu Leu Tyr Phe Gln Asp
                660                 665                 670

Gln Ala Ser Trp Thr Leu Glu Glu Leu Ser Lys Ala Val Lys Met Pro
        675                 680                 685

Val Ala Leu Leu Arg Arg Arg Met Ser Val Trp Leu Gln Gln Gly Val
        690                 695                 700

Leu Arg Glu Glu Pro Pro Gly Thr Phe Ser Val Ile Glu Glu Arg
705                 710                 715                 720

Pro Gln Asp Arg Asp Asn Met Val Leu Ile Asp Ser Asp Asp Glu Ser
                725                 730                 735

Asp Ser Gly Met Ala Ser Gln Ala Asp Gln Lys Glu Glu Leu Leu
                740                 745                 750

Leu Phe Trp Thr Tyr Ile Gln Ala Met Leu Thr Asn Leu Glu Ser Leu
        755                 760                 765

Ser Leu Asp Arg Ile Tyr Asn Met Leu Arg Met Phe Val Val Thr Gly
770                 775                 780

Pro Ala Leu Ala Glu Ile Asp Leu Gln Glu Leu Gln Gly Tyr Leu Gln
785                 790                 795                 800

Lys Lys Val Arg Asp Gln Gln Leu Val Tyr Ser Ala Gly Val Tyr Arg
                805                 810                 815

Leu Pro Lys Asn Cys Ser
            820

<210> SEQ ID NO 13
<211> LENGTH: 8
<212> TYPE: PRT
<213> ORGANISM: Artificial sequence
<220> FEATURE:
```

```
<223> OTHER INFORMATION: synthetic

<400> SEQUENCE: 13

Asp Tyr Lys Asp Asp Asp Asp Lys
1               5
```